United States Patent
Jovanovic et al.

(10) Patent No.: US 10,506,974 B2
(45) Date of Patent: Dec. 17, 2019

(54) HEADSETS AND ELECTRODES FOR GATHERING ELECTROENCEPHALOGRAPHIC DATA

(71) Applicant: The Nielsen Company (US), LLC, New York, NY (US)

(72) Inventors: Marko Jovanovic, Berlin (DE); Kashyap Fruitwala, Berlin (DE); Mohammad Moradi, Berlin (DE); Batia Bertho, Berlin (DE); Reimond Bausse, Fürth (DE); Mehran Mahinpour Tirooni, Berlin (DE); Yakob Badower, Berlin (DE)

(73) Assignee: THE NIELSEN COMPANY (US), LLC, New York, NY (US)

( * ) Notice: Subject to any disclaimer, the term of this patent is extended or adjusted under 35 U.S.C. 154(b) by 636 days.

(21) Appl. No.: 15/233,172

(22) Filed: Aug. 10, 2016

(65) Prior Publication Data
US 2017/0258400 A1    Sep. 14, 2017

Related U.S. Application Data

(60) Provisional application No. 62/312,953, filed on Mar. 24, 2016, provisional application No. 62/308,193, filed on Mar. 14, 2016.

(51) Int. Cl.
| | |
|---|---|
| *A61B 5/04* | (2006.01) |
| *A61B 5/00* | (2006.01) |
| *A61B 5/0478* | (2006.01) |

(52) U.S. Cl.
CPC .......... *A61B 5/6803* (2013.01); *A61B 5/0478* (2013.01); *A61B 5/6814* (2013.01);
(Continued)

(58) Field of Classification Search
CPC ... A61B 5/0478; A61B 5/0476; A61B 5/6803; A61B 5/6814; A61B 5/0484;
(Continued)

(56) References Cited

U.S. PATENT DOCUMENTS

| | | |
|---|---|---|
| 2,409,033 A | 10/1946 | Garceau |
| 2,549,836 A | 4/1951 | McIntyre et al. |

(Continued)

FOREIGN PATENT DOCUMENTS

| | | |
|---|---|---|
| DE | 102010005551 | 7/2011 |
| EP | 0217383 | 4/1987 |

(Continued)

OTHER PUBLICATIONS

European Patent Office, "Extended European Search Report," issued in connection with European Patent Application No. 17000413.9, dated Jul. 24, 2017, 8 pages.

(Continued)

*Primary Examiner* — Joseph A Stoklosa
*Assistant Examiner* — Brian M Antiskay
(74) *Attorney, Agent, or Firm* — Hanley, Flight & Zimmerman, LLC

(57) ABSTRACT

Example headsets and electrodes are described herein. Example electrode units described herein include a housing having a cavity defined by an opening in a side of the housing and an electrode. In some such examples, the electrode includes a ring disposed in the opening and an arm, where the arm has a first portion extending outward from the opening away from the housing and a second portion extending from an end of the first portion toward the housing and into the cavity, and the first and second portions connect at a bend.

20 Claims, 20 Drawing Sheets

(52) U.S. Cl.
CPC ..... *A61B 5/7203* (2013.01); *A61B 2562/0209* (2013.01); *A61B 2562/166* (2013.01); *A61B 2562/182* (2013.01); *A61B 2562/225* (2013.01)

(58) Field of Classification Search
CPC ..... A61B 5/165; A61B 5/0006; A61B 5/7264; A61B 5/4076; A61B 5/04004; A61B 5/4806; A61B 5/6804; G06F 3/015
USPC ................ 600/372, 378, 382–384, 386–393, 600/544–545; 607/115–118
See application file for complete search history.

(56) References Cited

U.S. PATENT DOCUMENTS

| | | |
|---|---|---|
| 3,490,439 A | 1/1970 | Rolston |
| 3,508,541 A | 4/1970 | Westbrook et al. |
| 3,572,322 A | 3/1971 | Wade |
| 3,901,215 A | 8/1975 | John |
| 3,998,213 A | 12/1976 | Price |
| 4,033,334 A | 7/1977 | Fletcher et al. |
| 4,213,463 A | 7/1980 | Osenkarski |
| 4,397,331 A | 8/1983 | Medlar |
| 4,417,592 A | 11/1983 | John |
| 4,537,198 A | 8/1985 | Corbett |
| 4,550,735 A | 11/1985 | Akamatsu et al. |
| 4,632,122 A | 12/1986 | Johansson et al. |
| 4,640,290 A | 2/1987 | Sherwin |
| 4,683,892 A | 8/1987 | Johansson et al. |
| 4,709,702 A | 12/1987 | Sherwin |
| 4,736,751 A | 4/1988 | Gevins et al. |
| 4,770,180 A | 9/1988 | Schmidt et al. |
| 4,800,888 A | 1/1989 | Itil et al. |
| 4,865,038 A | 9/1989 | Rich et al. |
| 4,899,753 A | 2/1990 | Inoue et al. |
| 4,936,306 A | 6/1990 | Doty |
| 4,955,388 A | 9/1990 | Silberstein |
| 4,967,038 A | 10/1990 | Gevins et al. |
| 5,024,235 A | 6/1991 | Ayers |
| 5,038,782 A | 8/1991 | Gevins et al. |
| 5,213,338 A | 5/1993 | Brotz |
| 5,273,037 A | 12/1993 | Itil et al. |
| 5,291,888 A | 3/1994 | Tucker |
| 5,293,867 A | 3/1994 | Oommen |
| 5,345,934 A | 9/1994 | Highe et al. |
| 5,355,883 A | 10/1994 | Ascher |
| 5,357,957 A | 10/1994 | Itil et al. |
| 5,406,956 A | 4/1995 | Farwell |
| 5,452,718 A | 9/1995 | Clare et al. |
| 5,479,934 A | 1/1996 | Imran |
| 5,518,007 A | 5/1996 | Becker |
| 5,740,812 A | 4/1998 | Cowan |
| 5,772,591 A | 6/1998 | Cram |
| 5,800,351 A | 9/1998 | Mann |
| 5,868,670 A | 2/1999 | Randell |
| 5,954,642 A | 9/1999 | Johnson et al. |
| 5,983,129 A | 11/1999 | Cowan et al. |
| 6,002,957 A | 12/1999 | Finneran |
| 6,128,521 A | 10/2000 | Marro et al. |
| 6,154,669 A | 11/2000 | Hunter et al. |
| 6,161,030 A * | 12/2000 | Levendowski ...... A61B 5/0478 600/383 |
| 6,171,239 B1 | 1/2001 | Humphrey |
| 6,175,753 B1 | 1/2001 | Menkes et al. |
| 6,233,472 B1 | 5/2001 | Bennett et al. |
| 6,301,493 B1 | 10/2001 | Marro et al. |
| 6,374,143 B1 | 4/2002 | Berrang et al. |
| 6,381,481 B1 | 4/2002 | Levendowski et al. |
| 6,510,340 B1 | 1/2003 | Jordan |
| 6,574,513 B1 | 6/2003 | Collura et al. |
| 6,598,006 B1 | 7/2003 | Honda et al. |
| 6,606,519 B2 | 8/2003 | Powell |
| 6,626,676 B2 | 9/2003 | Freer |
| 6,654,626 B2 | 11/2003 | Devlin et al. |
| 6,662,052 B1 | 12/2003 | Sarwal et al. |
| 6,708,051 B1 | 3/2004 | Durousseau |
| 6,757,556 B2 | 6/2004 | Gopinathan et al. |
| 6,915,148 B2 | 7/2005 | Finneran et al. |
| 6,950,698 B2 | 9/2005 | Sarkela et al. |
| 6,961,601 B2 | 11/2005 | Matthews et al. |
| 6,973,342 B1 | 12/2005 | Swanson |
| 7,130,673 B2 | 10/2006 | Tolvanen-Laakso et al. |
| 7,173,437 B2 | 2/2007 | Hervieux et al. |
| D565,735 S | 4/2008 | Washbon |
| 7,359,744 B2 | 4/2008 | Lee et al. |
| 7,443,693 B2 | 10/2008 | Arnold et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,715,894 B2 | 5/2010 | Dunseath et al. |
| 7,809,420 B2 | 10/2010 | Hannula et al. |
| 8,103,328 B2 | 1/2012 | Turner et al. |
| 8,112,141 B2 | 2/2012 | Wilson et al. |
| 8,239,030 B1 | 8/2012 | Hagedorn et al. |
| 8,285,355 B2 * | 10/2012 | Chen .................... A61B 5/0478 600/383 |
| 8,290,563 B2 | 10/2012 | Jin et al. |
| 8,326,396 B2 | 12/2012 | Picht et al. |
| 8,392,250 B2 | 3/2013 | Pradeep et al. |
| 8,392,251 B2 | 3/2013 | Pradeep et al. |
| 8,396,744 B2 | 3/2013 | Pradeep et al. |
| 8,457,709 B2 * | 6/2013 | Matthews ............ A61B 5/6843 600/372 |
| 8,467,133 B2 | 6/2013 | Miller |
| 8,477,425 B2 | 7/2013 | Border et al. |
| 8,548,554 B2 | 10/2013 | Popescu et al. |
| 8,548,852 B2 | 10/2013 | Pradeep et al. |
| 8,655,428 B2 | 2/2014 | Pradeep et al. |
| 9,060,671 B2 | 6/2015 | Badower et al. |
| 9,203,175 B1 | 12/2015 | Osa |
| 9,320,450 B2 | 4/2016 | Badower |
| 9,398,864 B2 | 7/2016 | Lawrence et al. |
| 2001/0056225 A1 | 12/2001 | DeVito |
| 2002/0182574 A1 | 12/2002 | Freer |
| 2002/0188216 A1 | 12/2002 | Kayyali et al. |
| 2004/0044382 A1 | 3/2004 | Ibrahim |
| 2004/0073129 A1 | 4/2004 | Caldwell et al. |
| 2004/0077934 A1 | 4/2004 | Massad |
| 2005/0043774 A1 | 2/2005 | Devlin et al. |
| 2005/0107716 A1 | 5/2005 | Eaton et al. |
| 2005/0113656 A1 | 5/2005 | Chance |
| 2005/0197556 A1 | 9/2005 | Stoler |
| 2005/0215916 A1 | 9/2005 | Fadem et al. |
| 2006/0189900 A1 | 8/2006 | Flaherty |
| 2006/0265022 A1 | 11/2006 | John et al. |
| 2006/0293608 A1 | 12/2006 | Rothman et al. |
| 2007/0031798 A1 | 2/2007 | Gottfried |
| 2007/0048707 A1 | 3/2007 | Caamano et al. |
| 2007/0055169 A1 | 3/2007 | Lee et al. |
| 2007/0067007 A1 | 3/2007 | Schulman et al. |
| 2007/0106170 A1 | 5/2007 | Dunseath, Jr. et al. |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0255127 A1 | 11/2007 | Mintz et al. |
| 2008/0027345 A1 | 1/2008 | Kumada et al. |
| 2008/0082019 A1 | 4/2008 | Ludving et al. |
| 2008/0127978 A1 | 6/2008 | Rubin et al. |
| 2008/0177197 A1 | 7/2008 | Lee et al. |
| 2008/0208072 A1 | 8/2008 | Fadem et al. |
| 2008/0211768 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0275359 A1 | 11/2008 | Mintz et al. |
| 2008/0294031 A1 * | 11/2008 | Wilson .................. A61B 5/0408 600/383 |
| 2008/0295126 A1 | 11/2008 | Lee et al. |
| 2008/0306398 A1 | 12/2008 | Uchiyama et al. |
| 2008/0312523 A1 | 12/2008 | Dunseath |
| 2009/0030762 A1 | 1/2009 | Lee et al. |

(56) References Cited

U.S. PATENT DOCUMENTS

| | | | |
|---|---|---|---|
| 2009/0069652 A1 | 3/2009 | Lee et al. | |
| 2009/0070798 A1 | 3/2009 | Lee et al. | |
| 2009/0105576 A1 | 4/2009 | Do et al. | |
| 2009/0112077 A1 | 4/2009 | Nguyen et al. | |
| 2009/0131764 A1 | 5/2009 | Lee et al. | |
| 2009/0133047 A1 | 5/2009 | Lee et al. | |
| 2009/0150919 A1 | 6/2009 | Lee et al. | |
| 2009/0156925 A1* | 6/2009 | Jin | A61B 5/0478 600/396 |
| 2009/0171181 A1* | 7/2009 | Kumada | A61B 5/0478 600/383 |
| 2009/0253996 A1 | 10/2009 | Lee et al. | |
| 2009/0259137 A1 | 10/2009 | Delic et al. | |
| 2010/0022821 A1 | 1/2010 | Dubi et al. | |
| 2010/0041962 A1 | 2/2010 | Causevic et al. | |
| 2010/0042012 A1 | 2/2010 | Alhussiny | |
| 2010/0060300 A1 | 3/2010 | Muller et al. | |
| 2010/0075532 A1 | 3/2010 | Copp-Howland et al. | |
| 2010/0125190 A1 | 5/2010 | Fadem | |
| 2010/0125219 A1 | 5/2010 | Harris et al. | |
| 2010/0145176 A1 | 6/2010 | Himes | |
| 2010/0198042 A1 | 8/2010 | Popescu et al. | |
| 2010/0274152 A1 | 10/2010 | McPeck et al. | |
| 2010/0331661 A1 | 12/2010 | Nakagawa | |
| 2011/0004089 A1 | 1/2011 | Chou | |
| 2011/0015503 A1 | 1/2011 | Joffe et al. | |
| 2011/0040202 A1 | 2/2011 | Luo et al. | |
| 2011/0046503 A1 | 2/2011 | Pradeep et al. | |
| 2011/0054288 A1 | 3/2011 | Besio | |
| 2011/0098593 A1 | 4/2011 | Low et al. | |
| 2011/0151728 A1 | 6/2011 | Astola | |
| 2011/0224569 A1 | 9/2011 | Isenhart et al. | |
| 2011/0224570 A1 | 9/2011 | Causevic | |
| 2011/0237923 A1 | 9/2011 | Picht et al. | |
| 2011/0248729 A2 | 10/2011 | Mueller et al. | |
| 2011/0257502 A1 | 10/2011 | Lee | |
| 2011/0257937 A1 | 10/2011 | Lee | |
| 2011/0282231 A1 | 11/2011 | Pradeep et al. | |
| 2011/0282232 A1 | 11/2011 | Pradeep et al. | |
| 2011/0319975 A1 | 12/2011 | Ho et al. | |
| 2012/0003862 A1 | 1/2012 | Newman et al. | |
| 2012/0036004 A1 | 2/2012 | Pradeep et al. | |
| 2012/0036005 A1 | 2/2012 | Pradeep et al. | |
| 2012/0054018 A1 | 3/2012 | Pradeep et al. | |
| 2012/0072289 A1 | 3/2012 | Pradeep et al. | |
| 2012/0108995 A1 | 5/2012 | Pradeep et al. | |
| 2012/0143020 A1* | 6/2012 | Bordoley | A61B 5/1114 600/301 |
| 2013/0024272 A1 | 1/2013 | Pradeep et al. | |
| 2013/0166373 A1 | 6/2013 | Pradeep et al. | |
| 2013/0185144 A1 | 7/2013 | Pradeep et al. | |
| 2013/0310676 A1* | 11/2013 | Jung | A61B 5/6803 600/383 |
| 2014/0051960 A1 | 2/2014 | Badower et al. | |
| 2014/0276183 A1 | 9/2014 | Badower | |
| 2015/0011857 A1 | 1/2015 | Henson et al. | |
| 2015/0257673 A1 | 9/2015 | Lawrence et al. | |
| 2015/0282760 A1 | 10/2015 | Badower et al. | |
| 2016/0007918 A1 | 1/2016 | Badower et al. | |

FOREIGN PATENT DOCUMENTS

| | | |
|---|---|---|
| FR | 2627975 | 9/1989 |
| GB | 1374658 | 11/1974 |
| JP | 2002-056500 | 2/2002 |
| JP | 2005261464 | 9/2005 |
| JP | 2006-305334 | 11/2006 |
| JP | 2011120866 | 6/2011 |
| JP | 2013166005 | 8/2013 |
| JP | 2013-240485 | 12/2013 |
| WO | 1997-040745 | 11/1997 |
| WO | 2008-109694 | 9/2008 |
| WO | 2008-109699 | 9/2008 |
| WO | 2011-055291 | 5/2011 |
| WO | 2011-056679 | 5/2011 |
| WO | 2012-036639 | 3/2012 |
| WO | 2013054498 | 4/2016 |

OTHER PUBLICATIONS

United States Patent and Trademark Office, "Non-Final Office Action", issued in connection with U.S. Appl. No. 15/233,168 dated Nov. 16, 2018, 41 pages.

European Patent Office, "Communication pursuant to Article 94(3) EPC," issued in connection with European Patent Application No. 17 000 413.9, dated Apr. 5, 2018, 5 pages.

Japanese Patent Office, "Notice of Reasons for Rejection", issued in connection with Japanese Patent Application No. 2017-047492, dated Jun. 5, 2018, 6 pages.

European Patent Office, "Communication Pursuant to Article 94(3) EPC", issued in connection with application No. 17 000 413.9 dated Jun. 11, 2019, 4 pages.

United States Patent and Trademark Offfice, "Non-Final Office Action", issued in connection with U.S. Appl. No. 15/233,179 dated Jul. 11, 2019, 56 pages.

United States Patent and Trademark Office, "Final Office Action", issued in connection with U.S. Appl. No. 15/233,168 dated Jun. 13, 2019, 11 pages.

El-Bab, et al., "Cognitive event related potentials during a learning task," Doctoral Dissertation, Faculty of Medicine, University of Southampton, 2001, 25 pages.

Gargiulo et al., "A Mobile EEG System With Dry Electrodes," (Nov. 2008), 4 pages.

Griss et al., "Characterization of micromachined spiked biopotential electrodes", IEEE Transactions on Biomedical Engineering, vol. 49, No. 6, Jun. 2002, 8 pages.

Picton, et al., "Guidelines for using human event-related potentials to study cognition: Recording standards and publication criteria," Psychophysiology, pp. 127-152, Society for Psychophysiological Research, 2000, 26 pages.

Sullivan et al., "A brain-machine interface using dry-contact, low-noise EEG sensors," In Proceedings of the 2008 IEEE International Symposium on Circuits and Systems, May 18, 2008, 4 pages.

Taheri, et al., "A dry electrode for EEG recording," Electroencephalography and clinical Neurophysiology, pp. 376-383, Elsevier Science Ireland Ltd., 1994, 8 pages.

Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, Nov. 2009, 12 pages.

Zyga, "A Baseball Cap That Can Read Your Mind," PhysOrg.com, located at www.physorg.com/news130152277.html, May 16, 2008, 11 pages.

China National Intellectual Property Administration, "First Office Action", issued in connection with application No. 201710304090.7 dated Sep. 19, 2019, 9 pages.

* cited by examiner

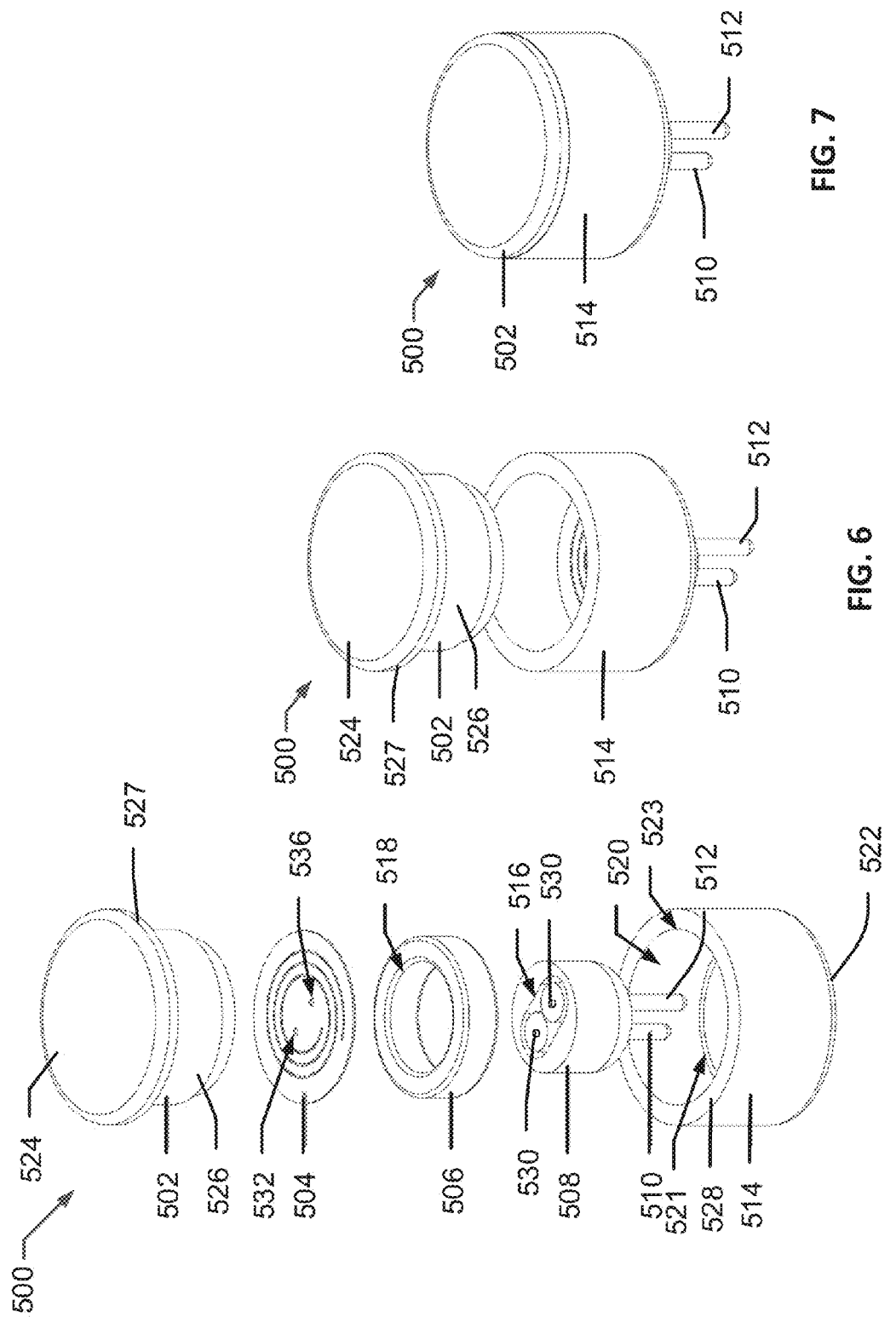

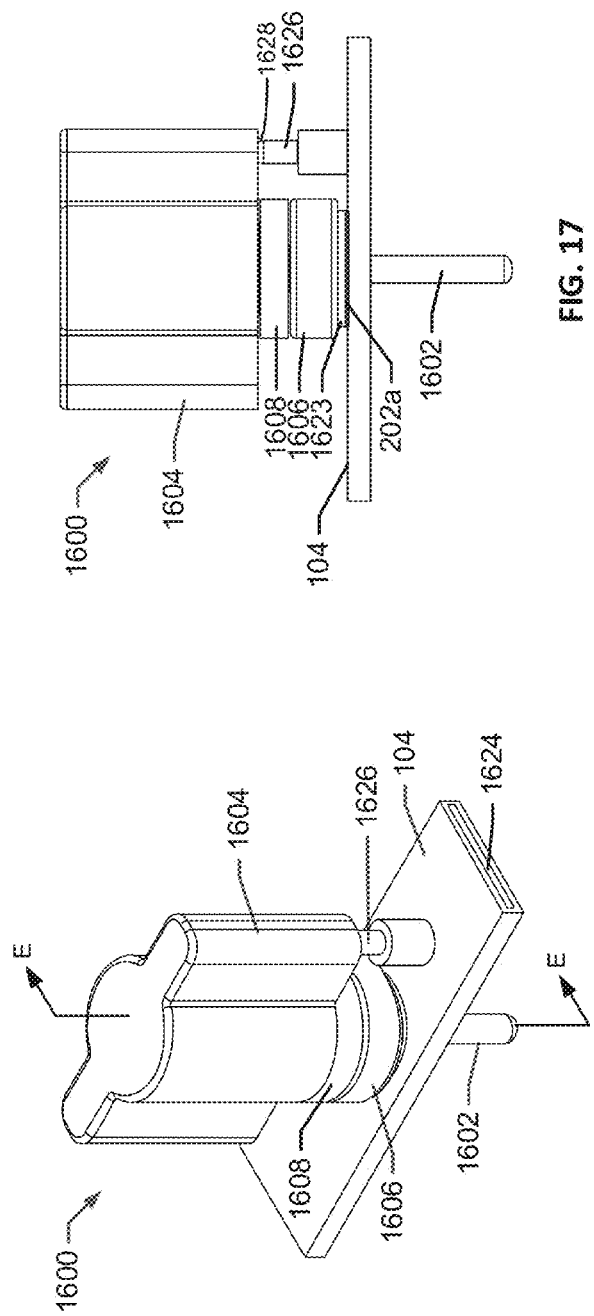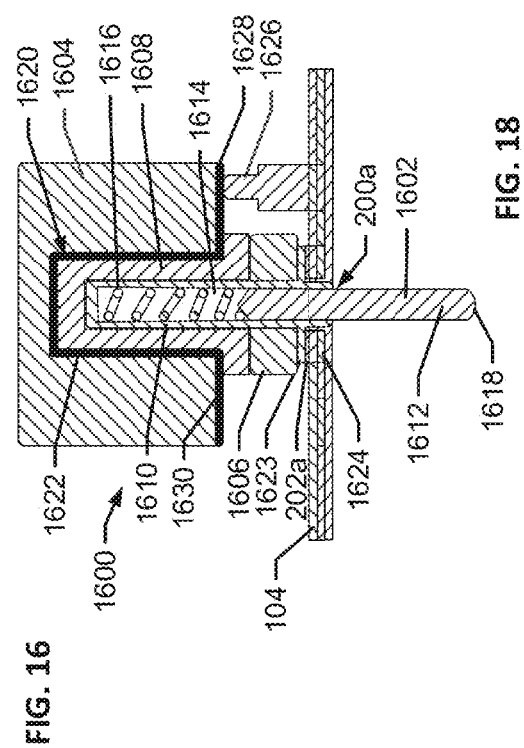

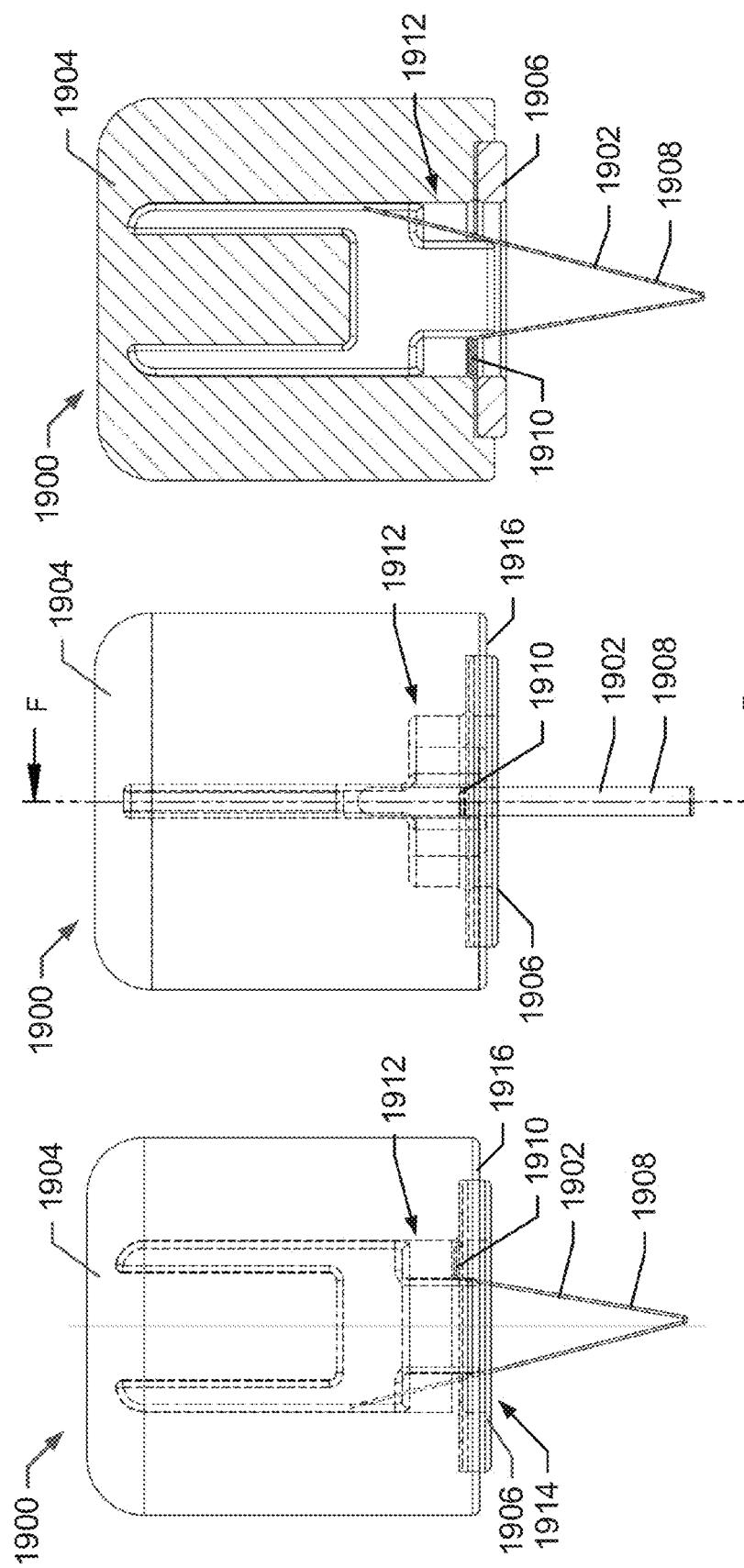

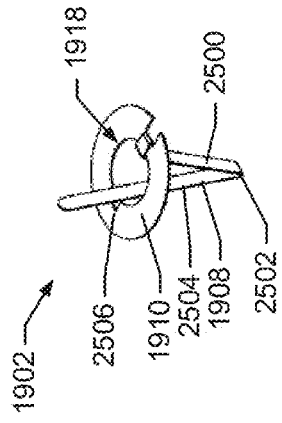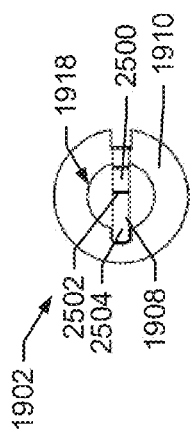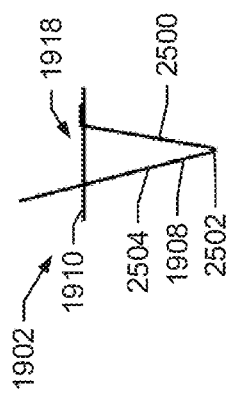
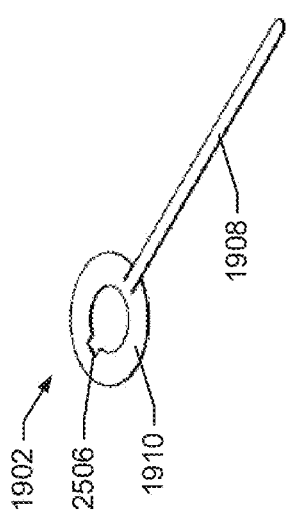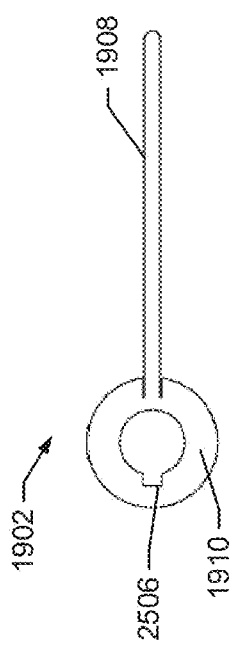

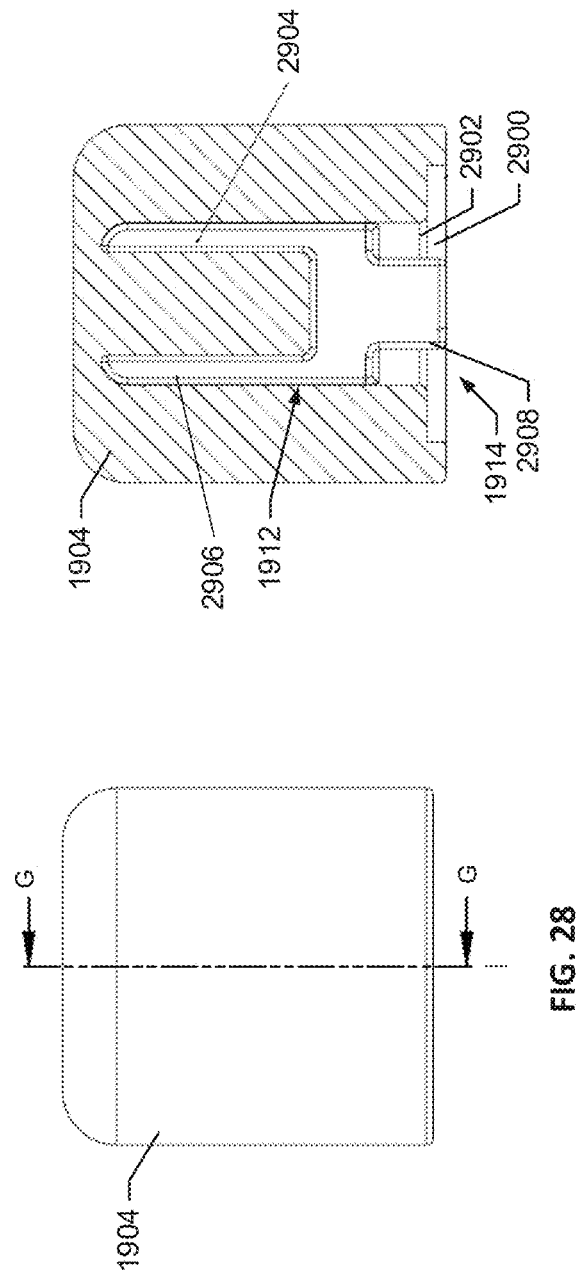
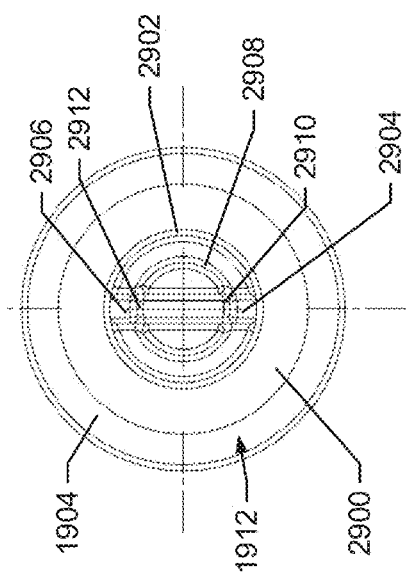
FIG. 30
FIG. 28
FIG. 29

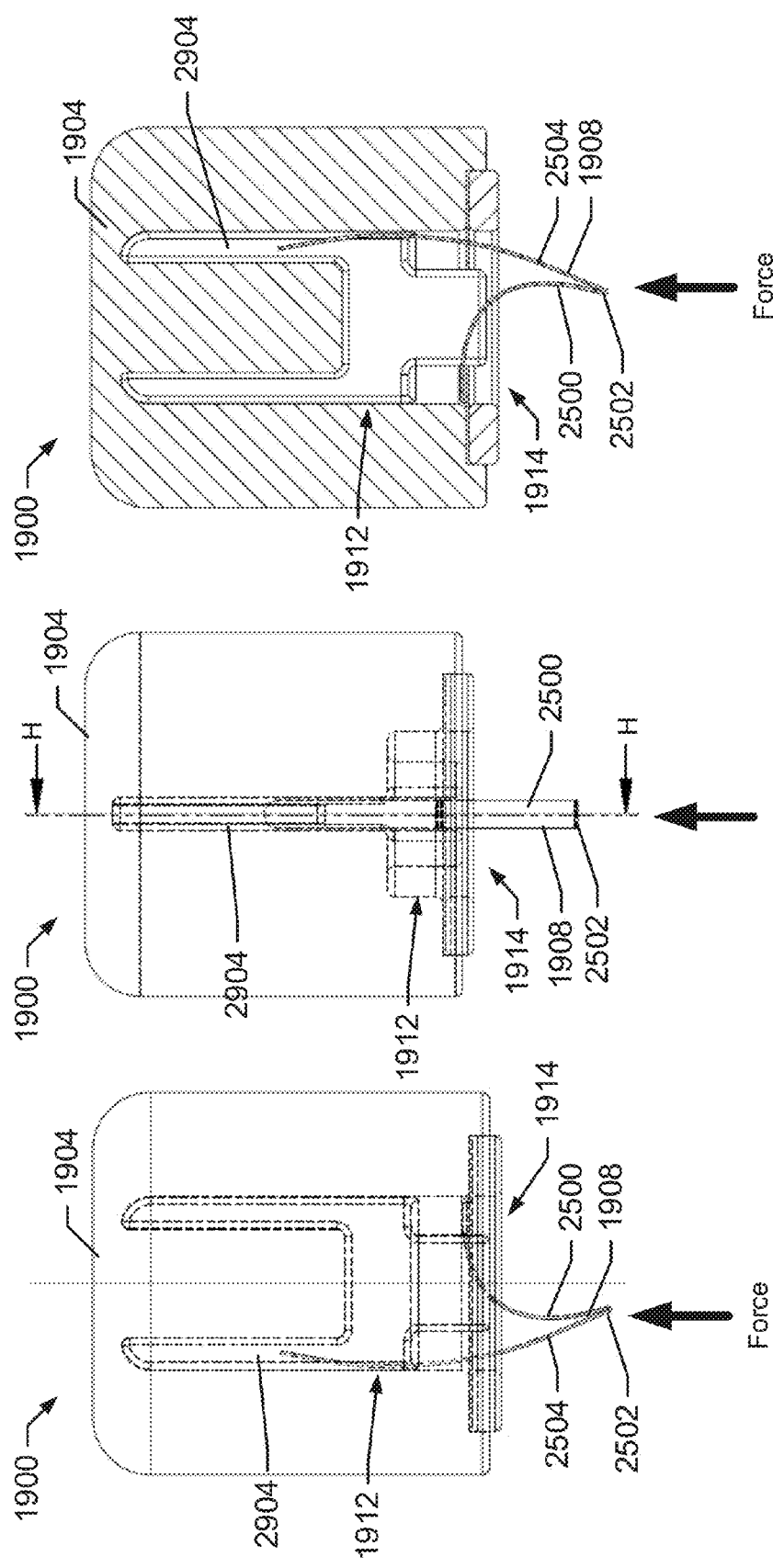

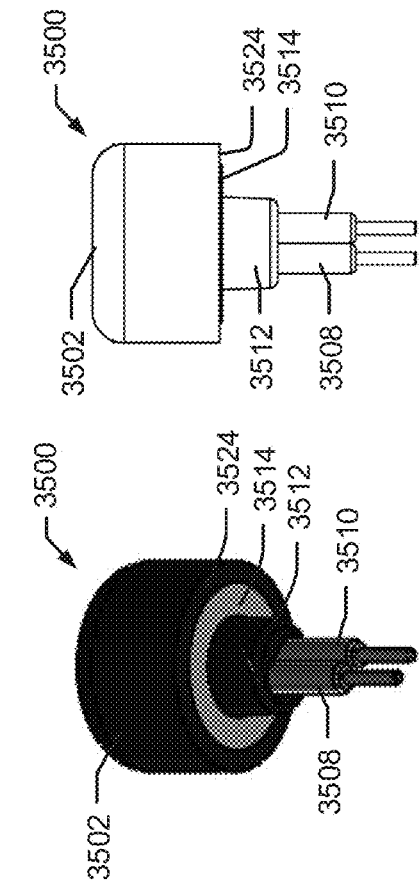
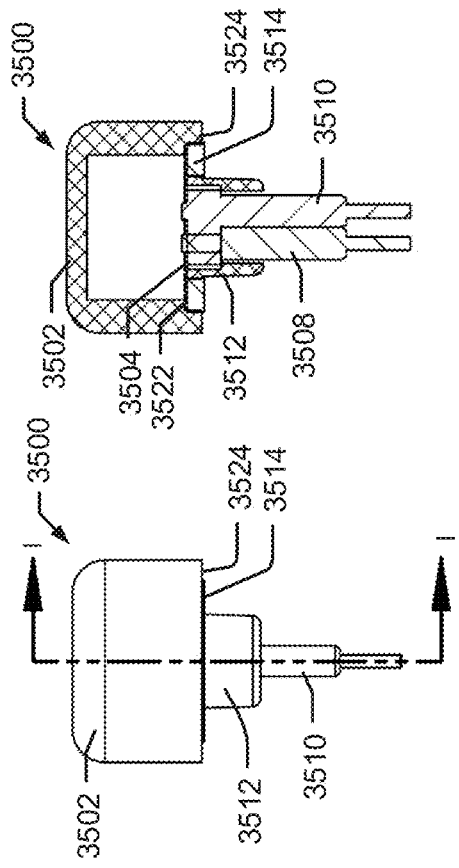
FIG. 37
FIG. 39
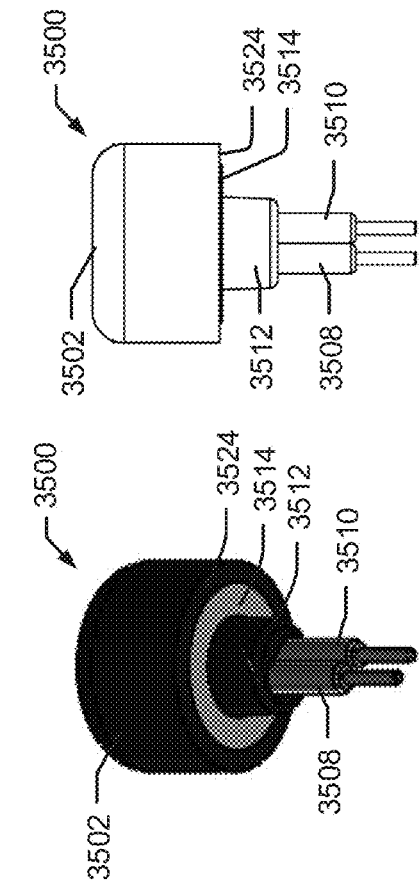
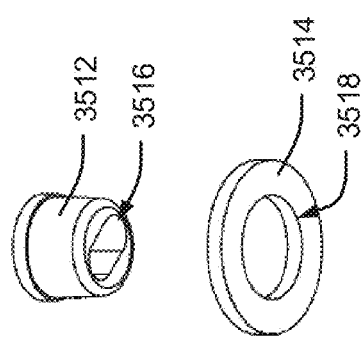
FIG. 36
FIG. 38
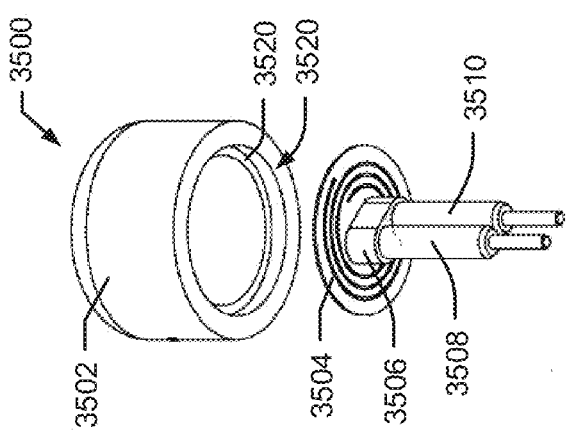
FIG. 35

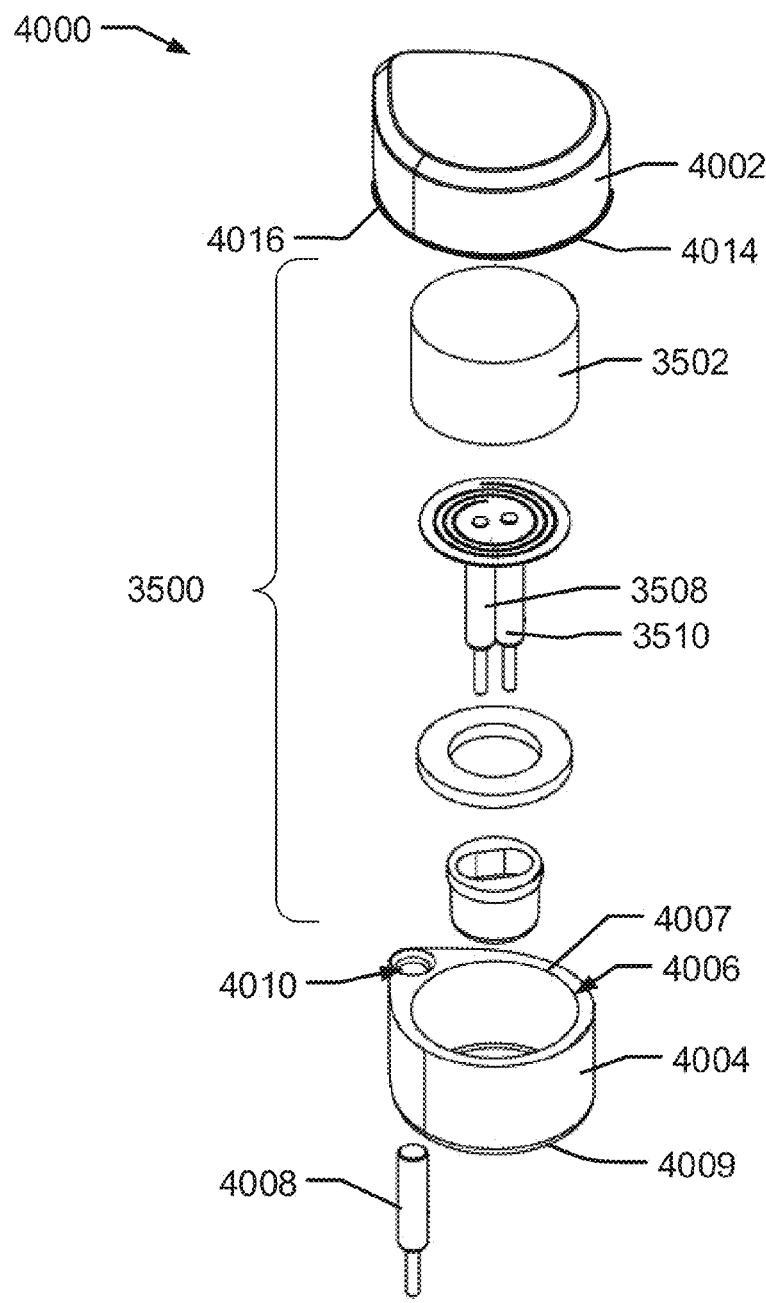
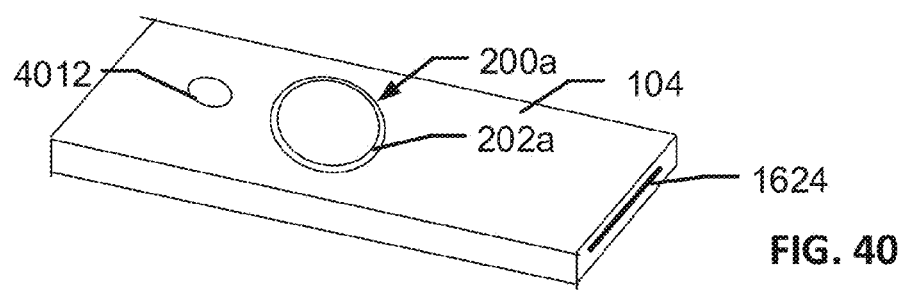
FIG. 40

HEADSETS AND ELECTRODES FOR GATHERING ELECTROENCEPHALOGRAPHIC DATA

RELATED APPLICATIONS

This application claims priority under 35 U.S.C. § 119(e) to U.S. Provisional Application No. 62/312,953, titled "Headsets and Electrodes for Gathering Electroencephalographic Data," filed Mar. 24, 2016. This application also claims priority under 35 U.S.C. § 119(e) to U.S. Provisional Application No. 62/308,193, titled "Headsets and Electrodes for Gathering Electroencephalographic Data," filed Mar. 14, 2016. U.S. Provisional Application Nos. 62/312,953 and 62/308,193 are hereby incorporated by this reference in their entireties.

FIELD OF THE DISCLOSURE

This disclosure relates generally to neurological and physiological monitoring and, more particularly, to headsets and electrodes for gathering electroencephalographic data.

BACKGROUND

Electroencephalography (EEG) involves measuring and recording electrical activity corresponding to neural processes in the brain. EEG data is typically measured using a plurality of electrodes placed on the scalp of a user to measure voltage fluctuations resulting from this electrical activity within the neurons of the brain.

BRIEF DESCRIPTION OF THE DRAWINGS

FIG. 5 is an exploded view of an example electrode unit having example electrodes that may be used with the example headset of FIG. 1.

FIG. 6 is a partially assembled view of the example electrode unit of FIG. 5.

FIG. 7 is an assembled view of the example electrode unit of FIG. 5.

FIG. 16 is a perspective view of another example electrode unit having an example electrode that may be used with the example headset of FIG. 1.

FIG. 17 is a side view of the example electrode unit of FIG. 16.

FIG. 18 is cross-sectional view of the example electrode unit of FIGS. 16 and 17 taken along line E-E of FIG. 16.

FIG. 19 is a side view of another example electrode unit having an example electrode that may be used with the example headset of FIG. 1.

FIG. 20 is another side view of the example electrode unit of FIG. 19.

FIG. 21 is a cross-sectional view of the example electrode unit of FIGS. 19 and 20 taken along line F-F of FIG. 20.

FIG. 22 is a perspective view of the example electrode of FIG. 19 in an unassembled state.

FIG. 23 is a top view of the example electrode of FIG. 22.

FIG. 24 is a side view of the example electrode of FIG. 22.

FIG. 25 is a perspective view of the example electrode of FIG. 19 in an assembled state.

FIG. 26 is a top view of the example electrode of FIG. 25.

FIG. 27 is a side view of the example electrode of FIG. 25.

FIG. 28 is a side view of an example housing of the example electrode unit of FIG. 19.

FIG. 29 is a bottom view of the example housing of FIG. 28.

FIG. 30 is a cross-sectional view of the example housing of FIGS. 28 and 29 taken along line G-G of FIG. 28.

FIG. 31 is a side view of the example electrode unit of FIG. 19 showing the example electrode in a compressed state.

FIG. 32 is another side view of the example electrode unit of FIG. 31.

FIG. 33 is a cross-sectional view of the example electrode unit of FIGS. 31 and 32 taken along line H-H of FIG. 32.

FIG. 35 is an exploded view of another example electrode unit having example electrodes that may be used with the example headset of FIG. 1.

FIG. 36 is an assembled view of the example electrode unit of FIG. 35.

FIG. 37 is a side view of the example electrode unit of FIG. 35.

FIG. 38 is another side view of the example electrode unit of FIG. 35.

FIG. 39 is a cross-sectional view of the example electrode unit of FIG. 35 taken along line I-I of FIG. 38.

FIG. 40 is an exploded view of an example shielding unit implemented with the example electrode unit of FIG. 35.

Figure 1:
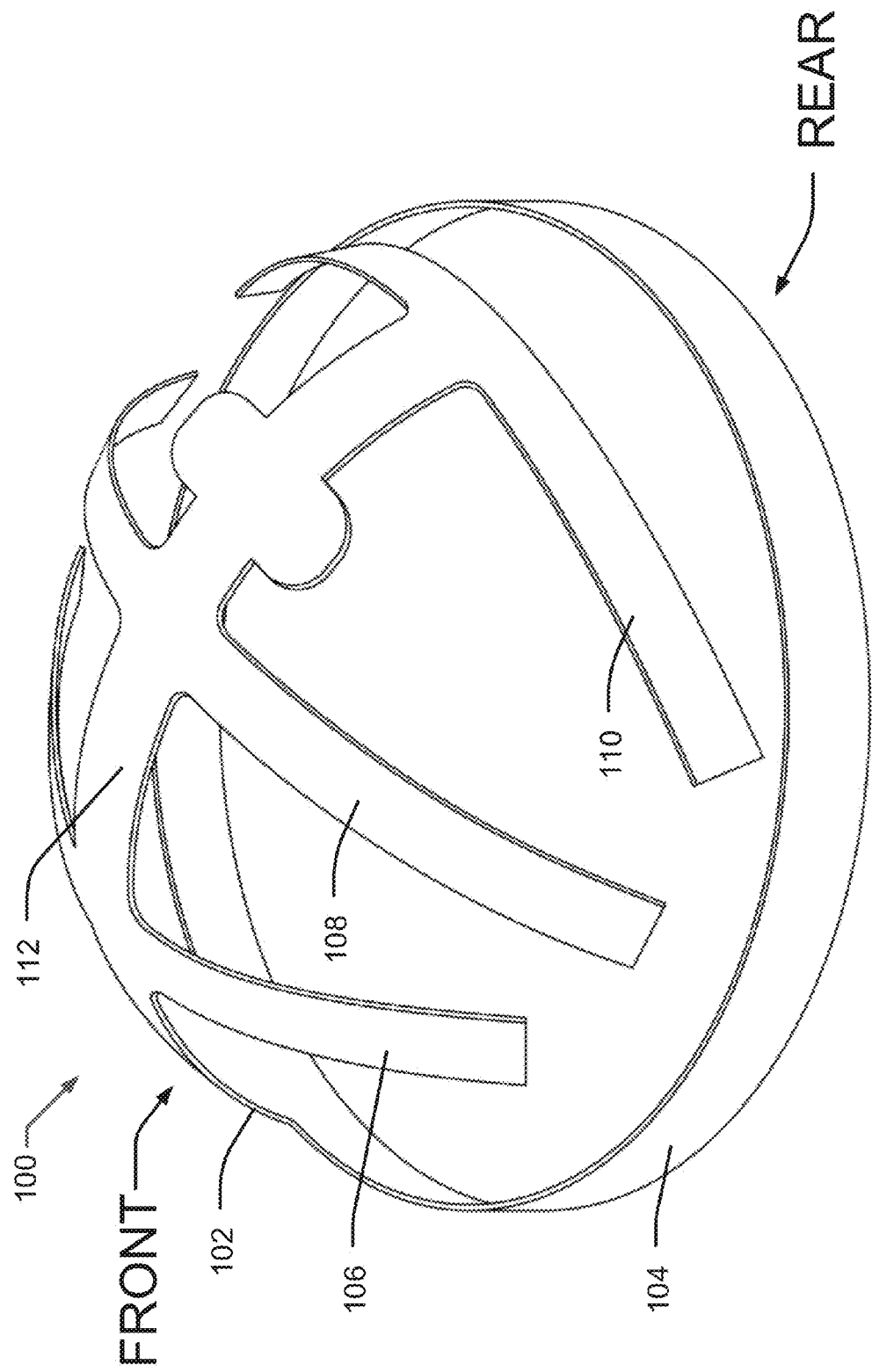
FIG. 1 is a perspective view of an example headset constructed in accordance with the teachings of this disclosure for gathering EEG signals.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

DETAILED DESCRIPTION

Example headsets disclosed herein may be used to obtain EEG signals from a brain in the head of a subject. Example headsets disclosed herein include electrode units that may be removably or permanently coupled to the headsets. In some examples, an electrode unit is magnetically couplable to an example headset. In other examples, the electrode units are coupled with mechanical fasteners to the headset such as, for example, a threaded connection or a friction fit. Example electrode units include one or more electrodes. In some examples, the electrode(s) include an electrode body and a pin that is retractable into the electrode body. In some such examples, the pin is biased outward via a spring. In some examples, the electrode(s) include an arm that is bendable or compressible.

Example electrode units disclosed herein include a guide defining an opening and an electrode disposed in the opening. In some such examples, the electrode has a housing, a first spring, and a pin, where the pin is biased outward from a first end of the housing via the first spring. In some examples, the electrode unit further includes a second spring disposed over the opening adjacent a second end of the housing.

In some examples, the electrode is a first electrode, the housing is a first housing and the pin is a first pin. In some such examples, the electrode unit further includes a second electrode disposed in the opening. In some examples, the second electrode includes a second housing, a third spring, and a second pin, where the second pin is biased outward from a first end of the second housing via the third spring. In some examples, the first electrode and the second electrode are independently adjustable via the first spring and the third spring. In some examples, the first electrode and the second electrode are simultaneously adjustable via the second spring.

In some examples, the housing is coupled to the second spring. In some such examples, the housing includes a protrusion extending through an aperture in the second spring, where the housing is coupled to the second spring via staking or press fit. In some examples, the opening is a first opening, and the electrode unit further includes a connector having a second opening. In some such examples, the guide is disposed in the second opening of the connector. The connector may be coupled to a band to be disposed over a head of a subject. In some examples, the connector is a magnet. In some examples, the guide is coupled to the connector via an interference fit. In some examples, the electrode unit further includes an electrode unit housing having a third opening defining a cavity, and the connector is disposed in the third opening. In some examples, the connector is substantially aligned with a bottom of the electrode unit housing, and the guide and the electrode extend from the bottom of the electrode unit housing. In some examples, the electrode is movable through the first opening of the guide into the cavity of the electrode unit housing. In some examples, the second spring is disposed over the connector and the guide in the second cavity. In some such examples, when the electrode moves into the cavity of the electrode unit housing, a center of the second spring flexes into the cavity. In some examples, the electrode unit includes a pusher disposed in the cavity, and an outer rim of the second spring is coupled between the pusher and the connector. In some examples, the pusher is inserted into the cavity from a fourth opening in the electrode unit housing opposite the third opening. In some examples, the electrode unit housing includes a ledge in the opening, wherein an outer rim of the second spring is coupled between the connector and the ledge. In some examples, an outer rim of the second spring remains in contact with the connector when the center of the second spring flexes into the cavity. In some examples, the second spring is a spiral spring plate.

Example electrode units disclosed herein include a housing defining a cavity, conductive paste disposed on an inner wall of the cavity and an electrode disposed in the cavity and spaced apart from the inner wall of the cavity. In some such examples, the electrode extends from the cavity, and the conductive paste is to shield the electrode from noise. In some examples, the electrode unit includes a layer of insulation disposed between the electrode and the housing.

Example headsets disclosed herein include the disclosed electrode unit and a band to be disposed over a head of a subject. In some such examples, the band has an aperture extending through the band. In some examples, the electrode unit is to be coupled to the band and extend through the aperture. In some examples, the headset includes a pin coupled to the band adjacent the aperture, and the pin is to engage a bottom of the housing. In some examples, the conductive paste is further disposed on the bottom of the housing. In some examples, the pin is electrically coupled to a shielding electrode to be placed on the head of the subject. In some such examples, the pin is electrically coupled to the shielding electrode via a printed circuit board disposed in the band. In some examples, the headset further includes a head band, and the shielding electrode is coupled to the head band to contact a forehead of the subject. In some examples, the electrode unit includes a first connector and the band includes a second connector, where the first connector may be removably coupled to the second connector. In some examples, the first connector is a magnet and the second connector is a metal. In some examples, the second connector is a metal ring disposed around the aperture.

Example shielding units are disclosed herein. An example shielding unit includes a bottom cover having an opening extending from a top side to a bottom side of the bottom cover. The example shielding unit also includes a top cover coupled to the top side of the bottom cover. Conductive paste is disposed on a bottom of the top cover. The example electrode unit further includes a pin disposed in a channel extending through the bottom cover, where the pin is in contact with the conductive paste on the top cover and extends from the bottom side of the bottom cover.

In some examples, the pin is a pogo-pin. In some such examples, the shielding unit further includes an electrode unit and the electrode unit is disposed in the opening in the bottom cover. In some examples, the electrode unit is coupled to the bottom cover via an interference fit. In some examples, the electrode unit includes an electrode extending from the bottom side of the bottom cover.

Example headsets disclosed herein include the disclosed shielding unit and a band to be disposed over a head of a subject. The band has an aperture extending through the band, and the shielding unit is coupled to the band and the electrode extends through the aperture. In some examples, the band includes an electrical pad adjacent the aperture, where the pin engages the electrical pad. In some examples, the electrical pad is electrically coupled to a shielding electrode to be placed on the head of the subject. In some examples, the pin is electrically coupled to the shielding electrode via printed circuit board disposed in the band.

Some example electrode units disclosed herein include a housing having a cavity defined by an opening in a side of the housing and an electrode. In some such examples, the electrode includes a ring disposed in the opening and an arm, where the arm has a first portion extending outward from the opening away from the housing and a second portion extending from an end of the first portion toward the housing and into the cavity, and the first and second portions connect at a bend.

In some examples, the first portion of the arm extends through the ring and outward from the opening away from the housing. In some such examples, the second portion of the arm extends through the ring and into the cavity. In some examples, the cavity includes a channel extending into the housing. In some such examples, the second portion of the arm is movable into the channel when a force is applied to the bend.

In some examples, the electrode unit includes a connector coupled to the housing around the opening to couple the housing to a band to be worn over a head of a subject. In some examples, the ring is coupled between the connector and the housing. In some such examples, the connector is a magnet. In some examples, the housing includes a guide, and the guide is to extend through the ring of the electrode to align the electrode in the housing. In some examples, the first portion is to move toward the second portion when a force is applied to the bend. In some examples, the ring and the arm are integral.

Example headsets disclosed herein include the disclosed electrode unit and a band to be disposed over a head of a subject. The band includes an aperture extending through the band, and the electrode unit is coupled to the band and the first portion of the arm extends through the aperture.

In some examples, the electrode unit includes a first connector and the band includes a second connector, where the first connector is removably coupled to the second connector. In some examples, the first connector is a magnet and the second connector is a metal. In some examples, the second connector is a metal ring disposed around the aperture.

Turning now to the examples illustrated in the figures, FIG. 1 shows an example headset 100 for gathering EEG signals from the head of a subject (e.g., a person). As used herein, a subject may be any person, user, viewer, participant and/or panelist. A panelist may be, for example, a user registered on a panel maintained by a ratings entity (e.g., an audience measurement company) that owns and/or operates a ratings entity subsystem. Traditionally, audience measurement entities (also referred to herein as "ratings entities") determine demographic reach for advertising and media programming based on registered panel members. That is, an audience measurement entity enrolls people that consent to being monitored into a panel. During enrollment, the audience measurement entity receives demographic information from the enrolling people so that subsequent correlations may be made between advertisement/media exposure to those panelists and different demographic markets. People become panelists via, for example, a user interface presented on the media device (e.g., via a website). People become panelists in additional or alternative manners such as, for example, via a telephone interview, by completing an online survey, etc. Additionally or alternatively, people may be contacted and/or enlisted using any desired methodology (e.g., random selection, statistical selection, phone solicitations, Internet advertisements, surveys, advertisements in shopping malls, product packaging, etc.).

In the illustrated example, the headset 100 includes a body having bands that are shaped to extend over a head of a subject. The body 102 includes a head band 104 that fits over the head of the subject. In the illustrated example, the head band 104 is a continuous ring. In the illustrated example, the body 102 includes a first band 106, a second band 108 and a third band 110 that are positioned to extend over the head of subject from the left to the right sides of the head. In the illustrated example, the first, second and third bands 106, 108, 110 are coupled to the head band 104 by a midline band 112. The midline band 112 extends from the head band 104 and is positioned to extend over the head of the subject from the front to the rear of the head, or from the back to the front of the head (e.g., along the midline), depending on the orientation the headset 100 is worn. In other examples, the headset 100 may be worn in other orientations (e.g., the front of the headset 100 may be positioned on the rear of the head). In some examples, the headset may include more or fewer bands. The number of bands, lengths of bands, shapes of bands, orientation of bands, etc. may be based on the desired number of channels from which EEG signals are to be gathered and/or the desired locations of measurement.

In some examples, electrodes are coupled to the body 102 of the headset. In some examples, electrodes are coupled to each of the head band 104, the first band 106, the second band 108, the third band 110 and the midline band 112. In other examples, only certain ones of the head band 104, the first band 106, the second band 108, the third band 110 and/or the midline band 112 include electrodes. The electrodes may be coupled to apertures formed in the body 102, as disclosed in further detail herein.

In the illustrated example of FIG. 1, the head band 104 forms a continuous ring. In other examples, the head band 104 may be divided or split, and two ends of the head band 104 may be coupled together. In some examples, the body 102 is a substantially unitary part or component (e.g., a monolithic structure formed in one piece in a mold). In other examples, the body 102 may be constructed of multiple parts or components that are coupled (e.g., fastened) together. In some examples, the body 102 of the headset 100 is silicone, rubber or plastic. In such examples, the body 102 is relatively flexible yet retains its general shape.

Figure 2:
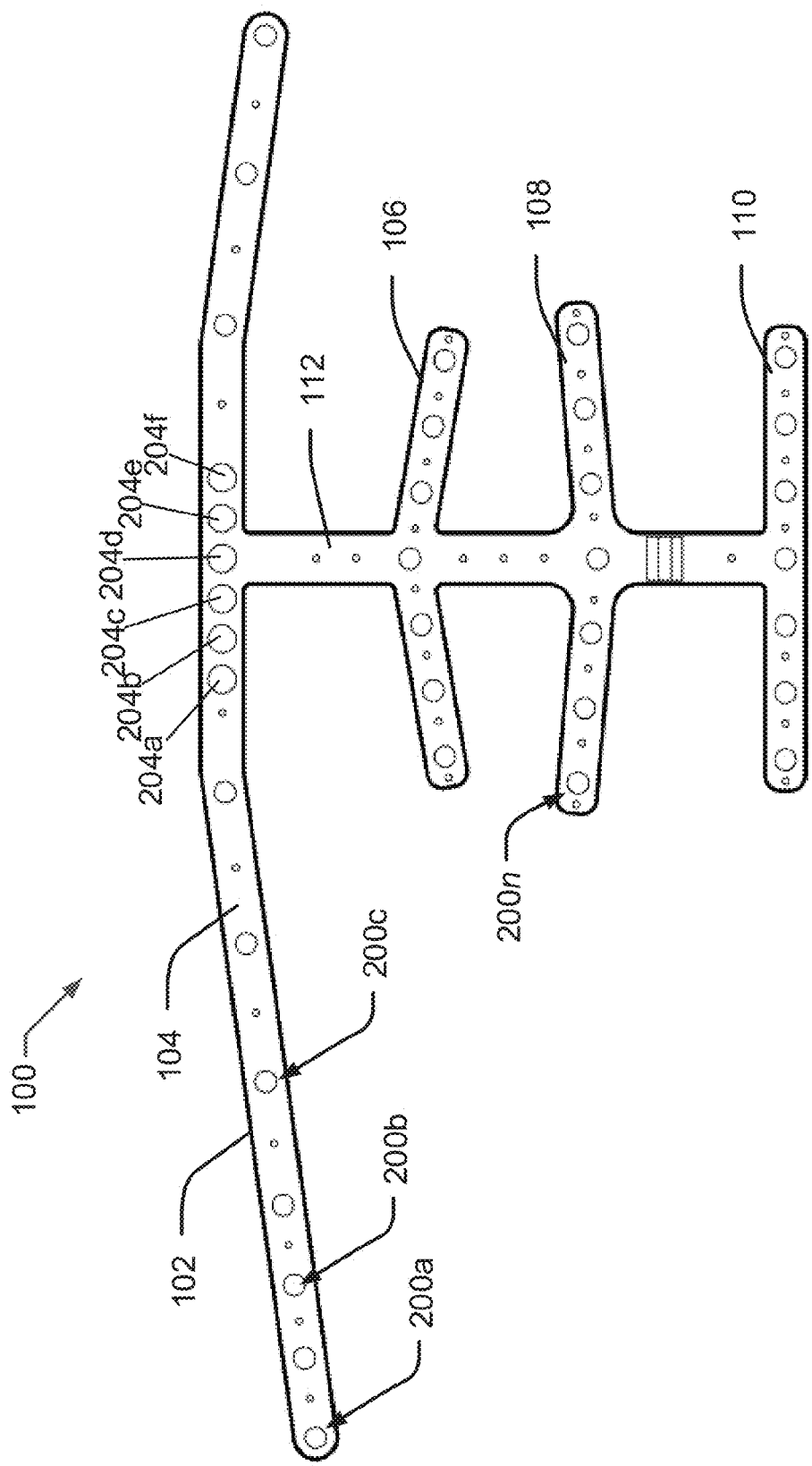
FIG. 2 is a plan view of one side (e.g., an inside) of the example headset of FIG. 1.
Figure 3:
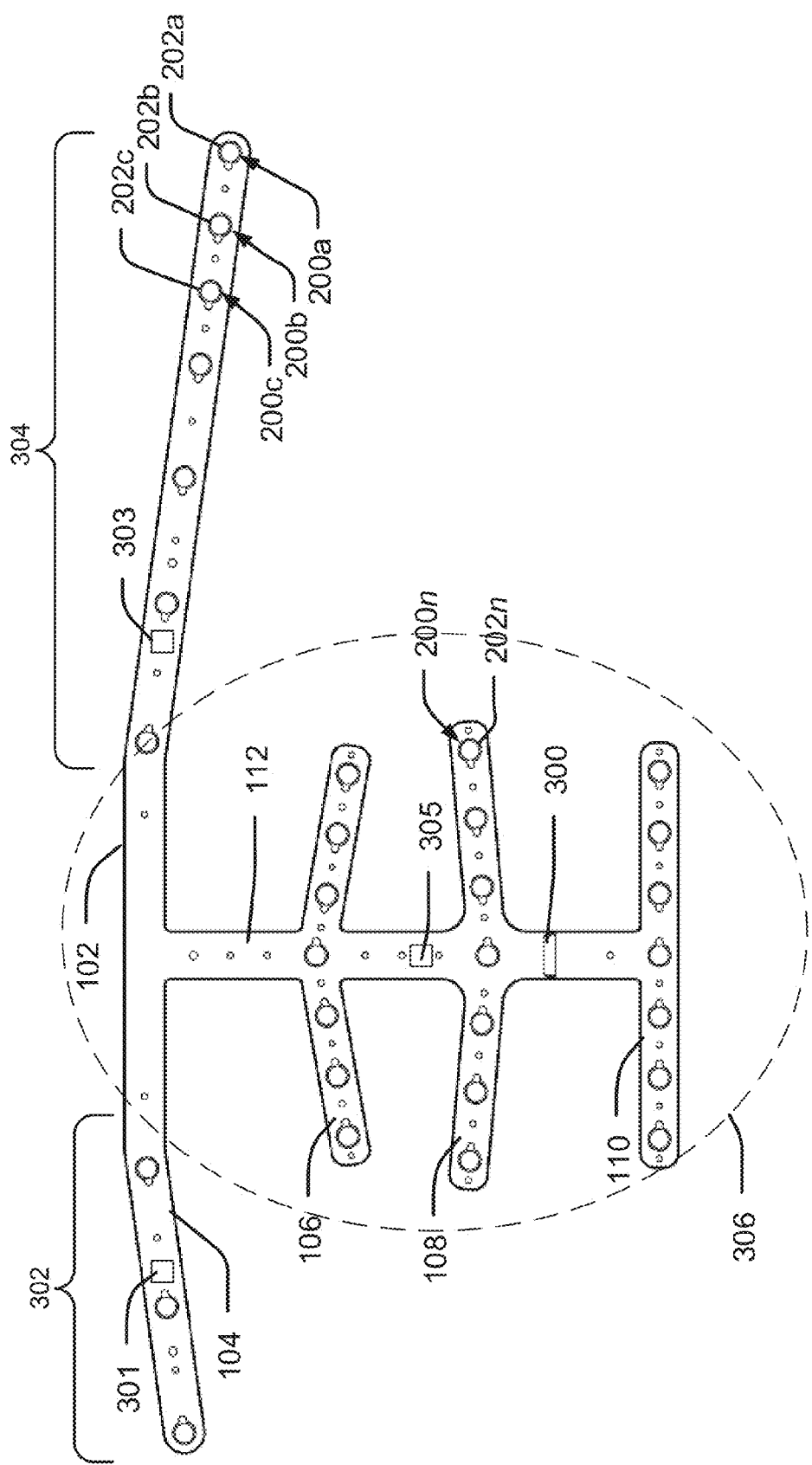
FIG. 3 is a plan view of another side (e.g., the outside) of the example headset of FIG. 1.

In some examples, the headset 100 includes apertures to receive electrodes. FIG. 2 shows a bottom, inside view of the body 102 of the example headset 100 in a flattened positioned, and FIG. 3 shows a top, outside view of the body 102 of the example headset 100 in a flattened position. In the illustrated example of FIGS. 2 and 3, the headset 100 includes a first aperture 200a (e.g., an opening, a hole, etc.) formed in the body 102 to receive an electrode. For example, an electrode (e.g., such as the electrode unit 500 of FIG. 5, disclosed in further detail here) may be coupled to the first aperture 200a. In some examples, the headset 100 includes a plurality of apertures for a plurality of electrodes, such as apertures 200b-200n. Any number (n) of apertures may be employed. The apertures 200a-200n may be formed in any of the head band 104, the first band 106, the second band 108, the third band 110 and/or the midline band 112.

To connect an electrode to the first aperture 200a, a first connector 202a is disposed adjacent the first aperture 200a, as illustrated in the example of FIG. 3. In some examples, the first connector 202a is a metal ring, and an electrode (or electrode unit) may include a magnet to couple the electrode (or electrode unit) to the first connector 202a. In other examples, the first connector 202a is magnetic. In other examples, other types of connectors (e.g., mechanical connectors) may be implemented. In the illustrated example, the first connector 202a encompasses or surrounds the first aperture 200a. In some examples, a plurality of connectors is used, and each of the connectors is associated with a respective one of the plurality of apertures 200a-200n. For example, a plurality of connectors 202a-202n is illustrated in FIG. 3 for the plurality of apertures 200a-200n. Although the illustrated example associates a connector with each aperture, fewer connectors than apertures may alternatively be used.

In some examples, the headset 100 includes a printed circuit board (PCB) (e.g., a substrate on which circuitry may be mounted and/or printed) disposed within the body 102. For example, silicone or another material may be molded around a PCB to form the body 102 of the headset 100. The PCB may be flexible and may include traces or wires to form circuitry. In some examples, the connectors 202a-202n (e.g., the wires or traces of the PCB) are in circuit with one or more of the apertures 200a-200n and/or an electrical connector 300 (FIG. 3), discussed in further detail herein. In some examples, the PCB is formed of one board. In other examples, the PCB may be constructed of multiple sections or portions and/or multiple PCBs may be employed. For example, as illustrated in FIG. 3, the headset 100 may include a first PCB 301 in a first part 302 of the head band 104, a second PCB 303 in a second part 304 of the head band 104 and a third PCB 305 in a third part 306 of the headset 100. In the illustrated example, the third part 306 includes a portion of the head band 104, the first band 106, the second band 108, the third band 110 and the midline band 112. The PCBs 301, 303, 305 may be in circuit (e.g., in electrical and/or magnetic connection) to form an overall circuit (or compound PCB) extending throughout the body 102 of the headset 100. In some examples, when multiple PCBs are used, relatively smaller PCBs or PCB sections can be cut from one piece of PCB material to thereby reduce waste compared to cutting the entire headset PCB in one piece. In other words, when cutting relatively smaller PCBs or PCB sections, the templates can be arranged closer together to minimize waste between adjacent pieces. In addition, in some examples, employing multiple PCBs results in increased adjustability and movement between sections of the head band 104, and avoids large areas of rigidity, which might be exhibited by a large PCB. Thus, employing multiple PCBs 301, 303, 305 increases comfort for the wearer of the headset 100.

Figure 4A:
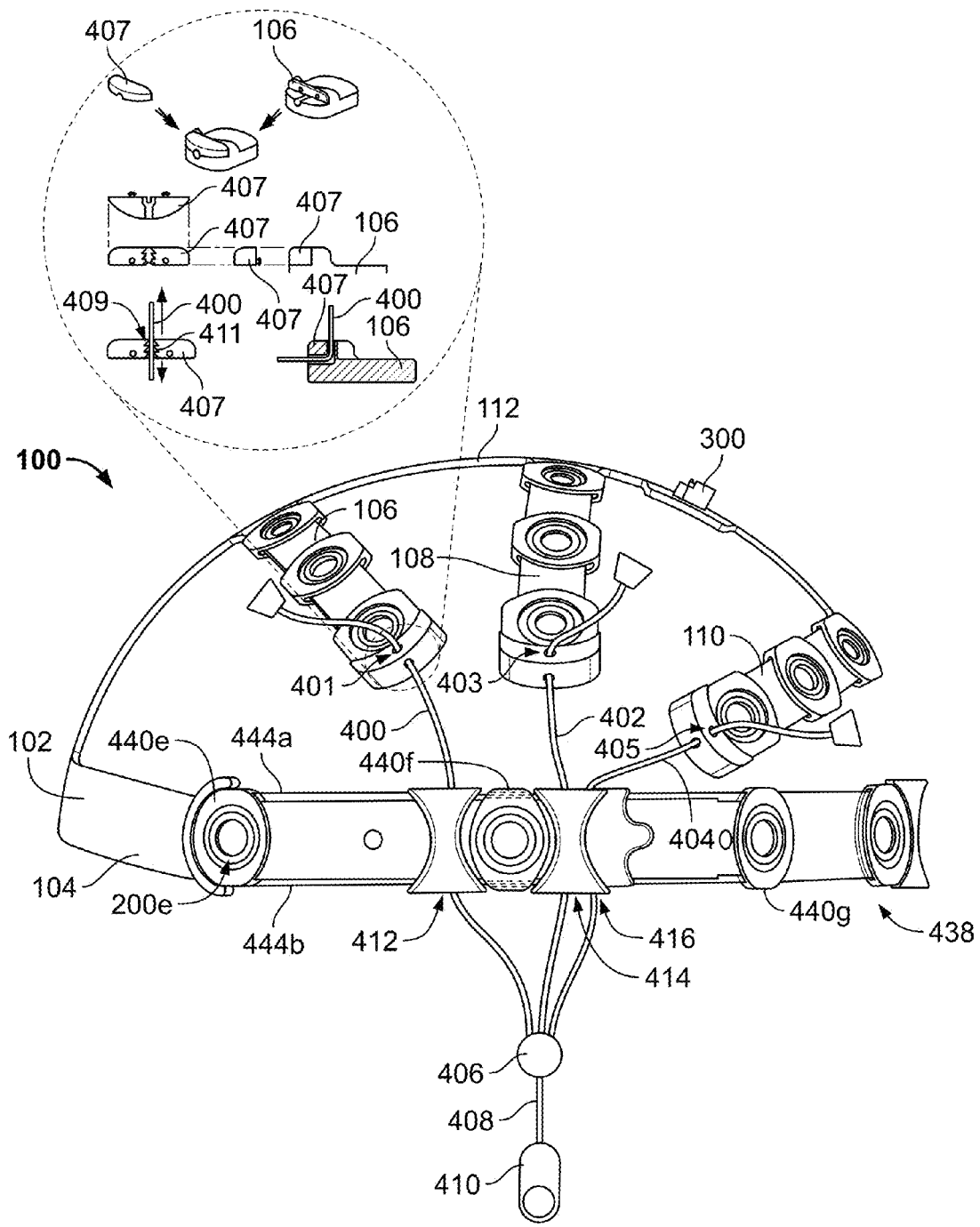
FIG. 4A is a left side view of the example headset of FIG. 1.

In some examples, the headset 100 may include one or more tension straps to tighten the headset 100 on the head of a subject. For example, FIG. 4A is a left side view of the example headset 100. A first tension strap 400 (e.g., a cord) is coupled to one end of the first band 106, a second tension strap 402 is coupled to one end of the second band 108, and a third tension strap 404 is coupled to one end of the third band 110. In some examples, the first, second and third tension straps 400, 402, 404 are elastic (e.g., rubber and/or silicone). The first, second and third tension straps 400, 402, 404 are coupled to a cover 406 (e.g., a connector). In the illustrated example, a pull strap 408 is coupled between the cover 406 and a first connector 410. The first connector 410 may be pulled to tighten the first, second and third tension straps 400, 402, 404 and, thus, to tighten the first, second and third bands 106, 108, 110 over the head of a subject. In the illustrated example, the cover 406 operates as connector or joiner where the straps 400, 402, 404, 408 are coupled. In other examples, the straps 400, 402, 404, 408 are coupled to each other and the cover 406 covers the connection. The first connector 410 couples to another connector extending from the right side of the headset 100 (disclosed in further detail herein). Therefore, the first, second and/or third bands 106, 108, 110 may be tightened or loosened together (e.g., simultaneously) by, for example, pulling or relaxing the pull strap 408. Additionally or alternatively, the first, second and/or third bands 106, 108, 110 may be independently adjusted. For example, as illustrated in FIG. 4A, the first tension strap 400 extends through a first opening 401 in the first band 106 (e.g., adjacent the end of the first band 106). The first opening 401 is dimensioned to create friction between the first band 106 and the first tension strap 400. The friction force is sufficient to couple the first tension strap 400 to the first band 106 when pulling the cover 406, for example. To shorten the effective length of the first tension strap 400 (e.g., the length of the first tension strap 400 between the end of the first band 106 and the cover 406), the end of the first tension strap 400 may be pulled (with sufficient force to overcome the friction) to slide the first tension strap 400 through the first opening 401. To lengthen or loosen the effective length of the first tension strap 400, the first tension strap 400 can be pulled from the opposite side of the first band 106. In some examples, teeth are provided in the first opening 401. An example assembly and cross-sectionals views are shows in the enlarged portion of FIG. 4A. In the illustrated example, an end cap 407 is coupled to the end of the first band 16. The end cap includes a passage 409 having teeth 411. The teeth 411 are angled to create friction against the first tension strap 400 when pulling the first tension strap 400 toward the head band 104 to loosen the first tension strap 400. Similar to the first opening 401, the second band 108 includes a second opening 403 through which the second tension strap 402 extends, and the third band 110 includes a third opening 405 through which the third tension strap 404 extends. Therefore, the first, second and third tensions straps 400, 402, 404 may be adjusted independently of each other.

In some examples, the head band 104 includes one or more passageways for the first, second and/or third tension straps 400, 402, 404. For example, as illustrated in FIG. 4A, a first passageway 412 (e.g., a channel, a through-hole, etc.) is provided in the head band 104. The first tension strap 400 extends through the first passageway 412. In the illustrated example, a second passageway 414 and a third passageway 416 are similarly provided for the second and third tension straps 402, 404. In some examples, two or more of the first, second and/or third tension straps 400, 402, 404 extend through the same passageway.

Figure 4B:
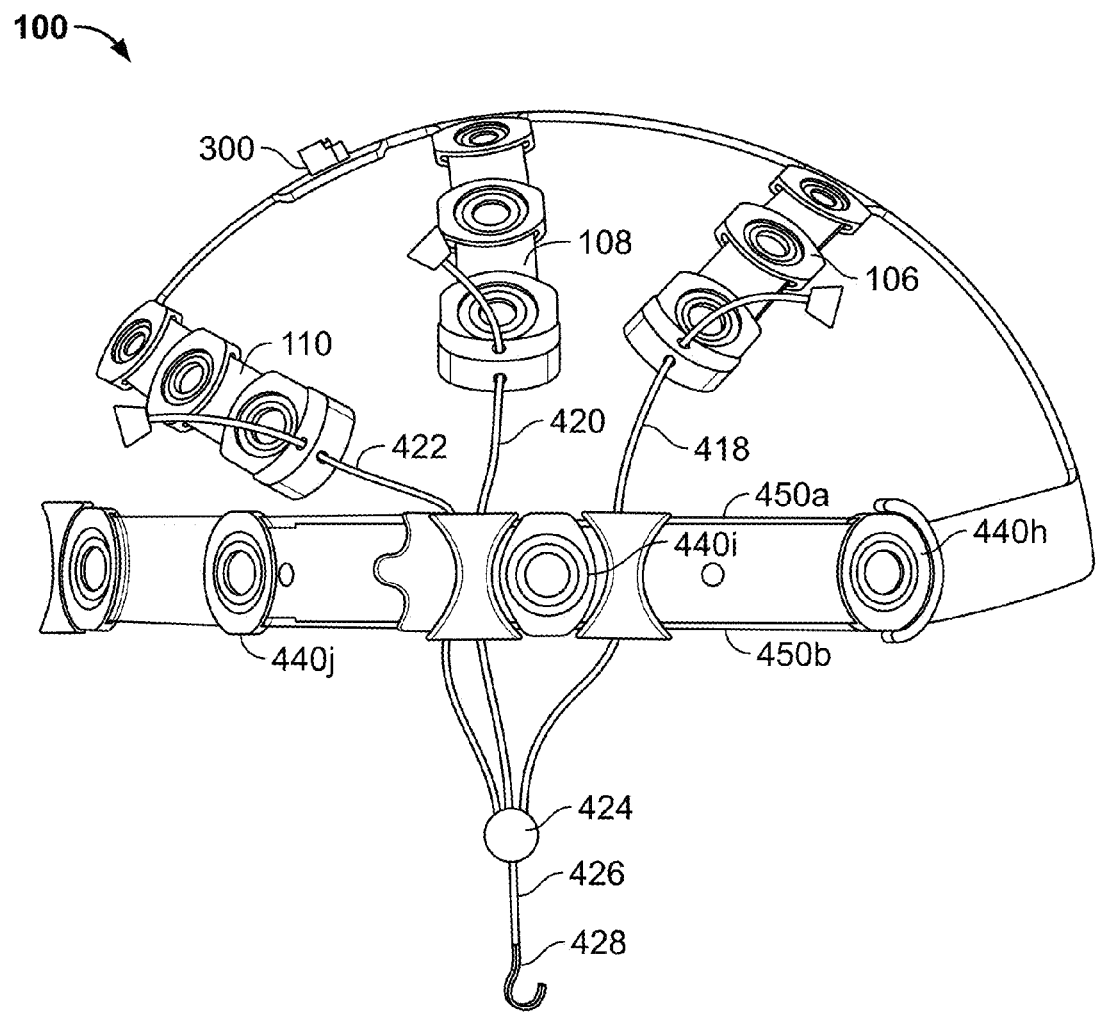
FIG. 4B is a right side view of the example headset of FIG. 1.

FIG. 4B is a right side view of the example headset 100. Similar to the left side (see FIG. 4A), the right side includes a fourth tension strap 418 (e.g., a cord), which may be coupled to the other end of the first band 106 opposite the first tension strap 400 (FIG. 4A), a fifth tension strap 420 coupled to the other end of the second band 108 opposite the second tension strap 402 (FIG. 4A), and a sixth tensions strap 422 coupled to the other end of the third band 110 opposite the third tension strap 404 (FIG. 4A). The fourth, fifth and sixth tension straps 418, 420, 422 are coupled to a second cover 424. Similar to the passageways 412, 414, 416 (FIG. 4A), the headset 100 includes one or more passageways for the fourth, fifth and/or sixth tension straps 418, 420, 422. In the illustrated example, a pull strap 426 is coupled between the second cover 424 and a second connector 428. In the illustrated example, the cover 406 operates as connector or joiner where the straps 418, 420, 422, 426 are coupled. The second connector 428 may be pulled to tighten the fourth, fifth and sixth tension straps 418, 420, 422 and, thus, to tighten the first, second and third bands 106, 108, 110 over the head of a subject. Also, similar to the first, second and third tension straps 400, 402, 404, the fourth, fifth and sixth tension straps 418, 420, 422 are independently adjustable by sliding the tension straps 418, 420, 422 through the respective openings to increase or decrease the effective length of the respective straps 418, 420, 422.

Figure 4C:
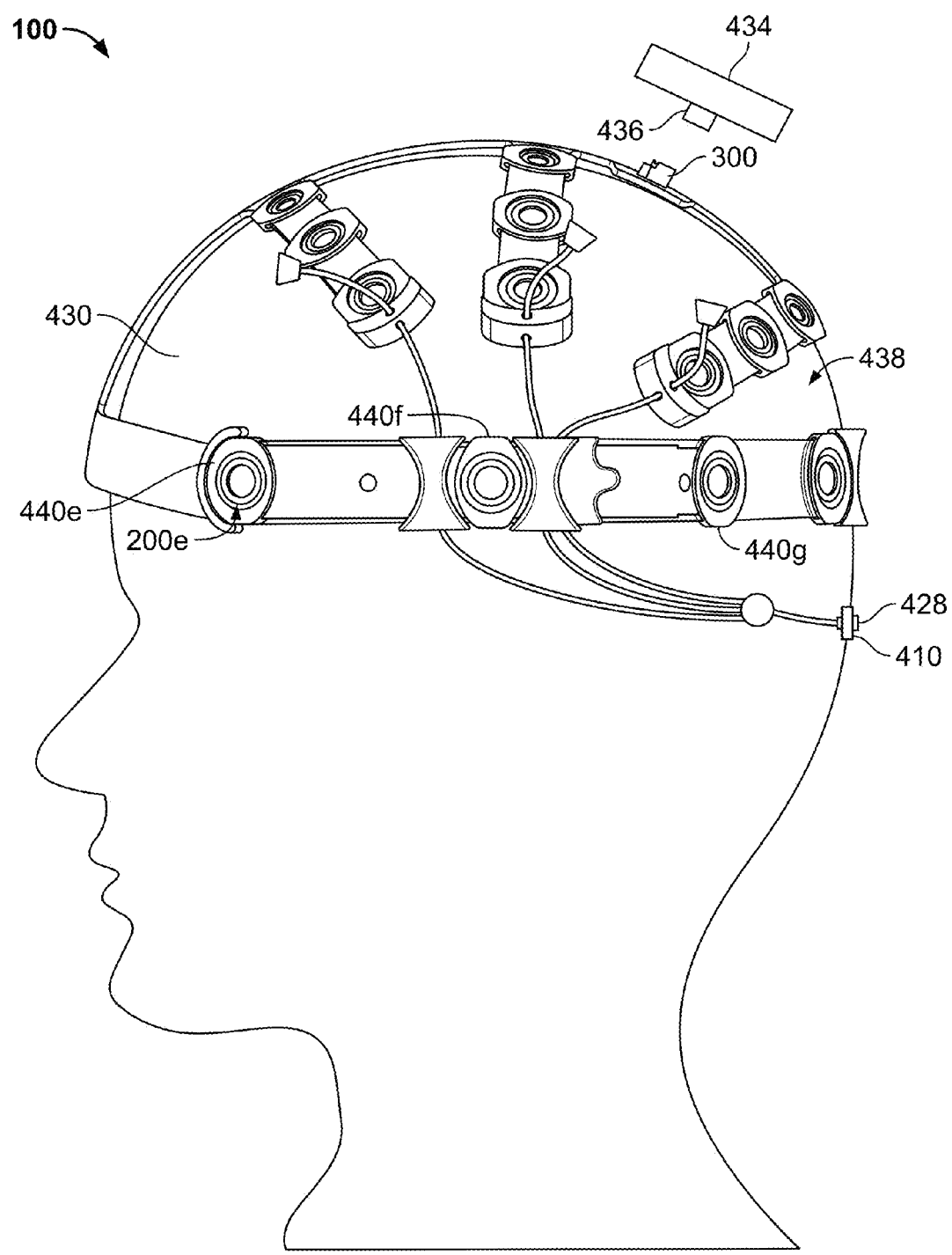
FIG. 4C illustrates the example headset of FIG. 1 on a head of a subject.

In some examples, the first connector 410 (FIG. 4A) and the second connector 428 (FIG. 4B) may be pulled taut and coupled to each other (e.g., beneath the chin of the wearer, behind the head of the wearer, etc.) to retain the headset 100 to a head of a subject. For example, FIG. 4C illustrates the example headset 100 on a head 430 of a subject. The first connector 410 is coupled to the second connector 428 at a rear of the head 430. In the illustrated example, the first connector 410 is implemented as a loop and the second connector 428 is implemented as a hook. In other examples, the first and second connectors 410, 428 may be other types of connectors, such as a button, a snap, a magnet, Velcro®, and/or any other suitable fastener. In other examples, the first and second connectors 410, 428 are connected under a chin of the subject.

In the illustrated example of FIGS. 4A-4C, the headset 100 includes the electrical connector 300 to which a processor (e.g., a controller, a microprocessor, a central processing unit (CPU), an application-specific integrated circuit (ASIC) or the like) can be connected. As disclosed above, the headset 100 may include one or more PCBs disposed within the body 102 (e.g., integrated within the body 102). The PCB(s) include traces or wires that communicatively couple one or more electrode(s) positioned in respective ones of the apertures 200a-200n to the electrical connector 300. As such, signals gathered by the electrodes are transmitted to the processor for collection and/or analysis. An example processor 434 is illustrated in FIG. 4C. The example processor 434 includes an electrical connector 436 that can be plugged into the electrical connector 300. In some examples, the processor 434 conditions the signals, filters/attenuates noise, provides additional signal processing and/or signal analysis and/or outputs data to an external device. In some examples, the processor 434 includes a transmitter to transmit signals gathered by the electrodes and/or data based on such signals.

Figure 4D:
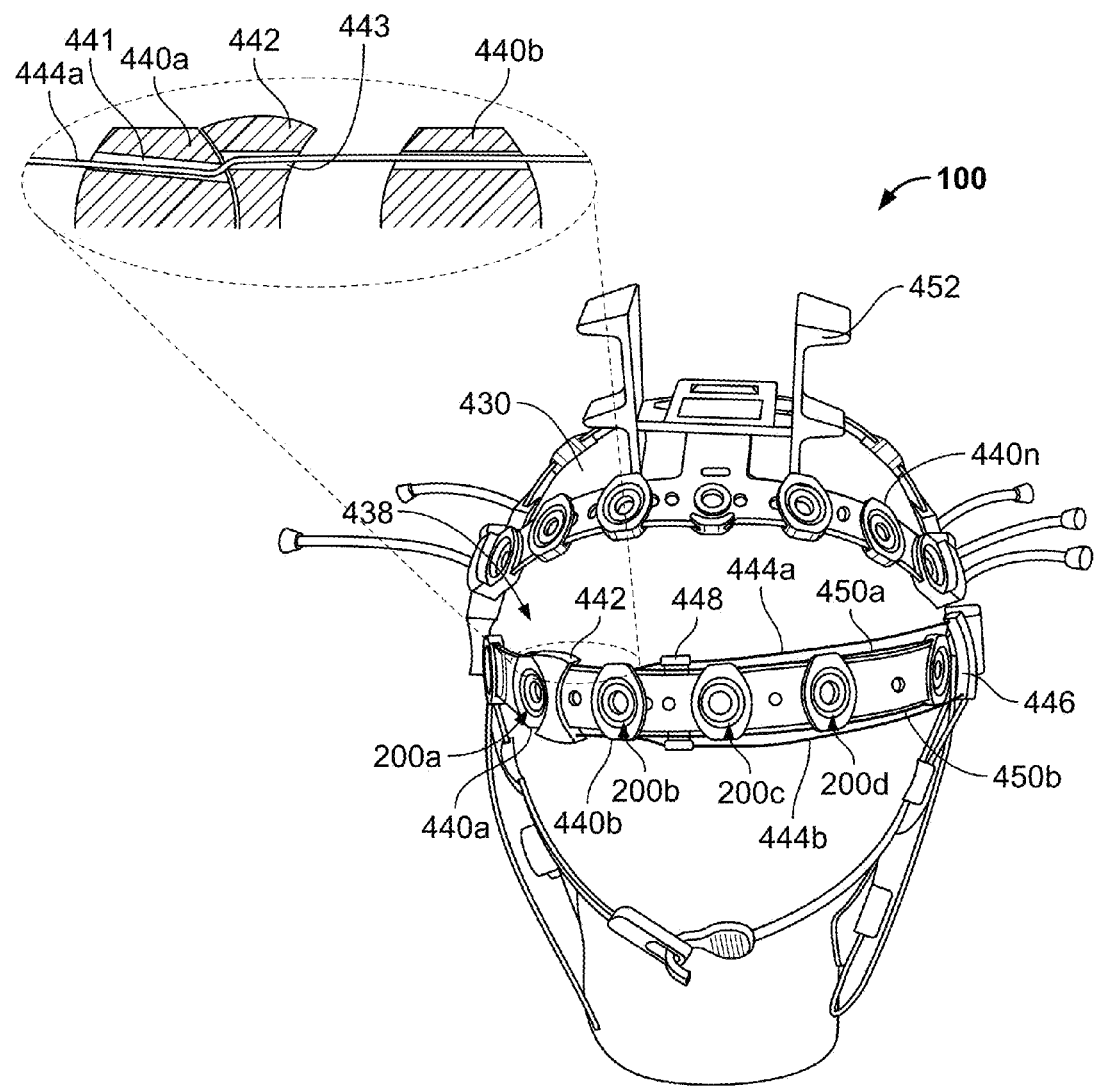
FIG. 4D is a rear view of the example headset of FIG. 1 disposed on a relatively small head.

In the illustrated example of FIGS. 4A-4C, the two ends of the head band 104 are coupled together via a latch or lock 438. As illustrated in FIGS. 2 and 3, the head band 104 is divided into the first part 302 and the second part 304, which extend from the midline band 112. The first part 302 is shorter than the second part 304. As such, the lock 438 connecting the ends of the first and second parts 302, 304 is offset from a rear of the head 430 of the subject (e.g., not position in the middle of the back of the head 430). Therefore, one or more electrodes can be positioned on the rear section of the head band 104 along the rear of the head 430, which is beneficial to gather EEG signals that are generated along the midline of the head near the rear or inion. For example, FIG. 4D shows a rear view of the headset 100 on a relatively small head. In the illustrated example, the back of the head band 104 includes four apertures (and connectors) where electrodes can be connected (and gather signals). In particular, the head band 104 includes the first aperture 200a, the second aperture 200b, the third aperture 200c and a fourth aperture 200d. In the illustrated example, the third aperture 200c is located along (or near) the midline of the head 430. Thus, in this instance, the third aperture 200c may be used with an electrode to gather signals from the midline of the head 430. The second aperture 200b, which is to the left of the midline, and the fourth aperture 200d, which is to the right of the midline, may be used with electrodes to gather signals to the immediate left and right, respectively, of the midline. Therefore, the midline, the left midline and the right midline locations may be accessed by electrodes. In some examples, the first aperture 200a may be left empty (no electrode inserted) or not activated.

Figure 4E:
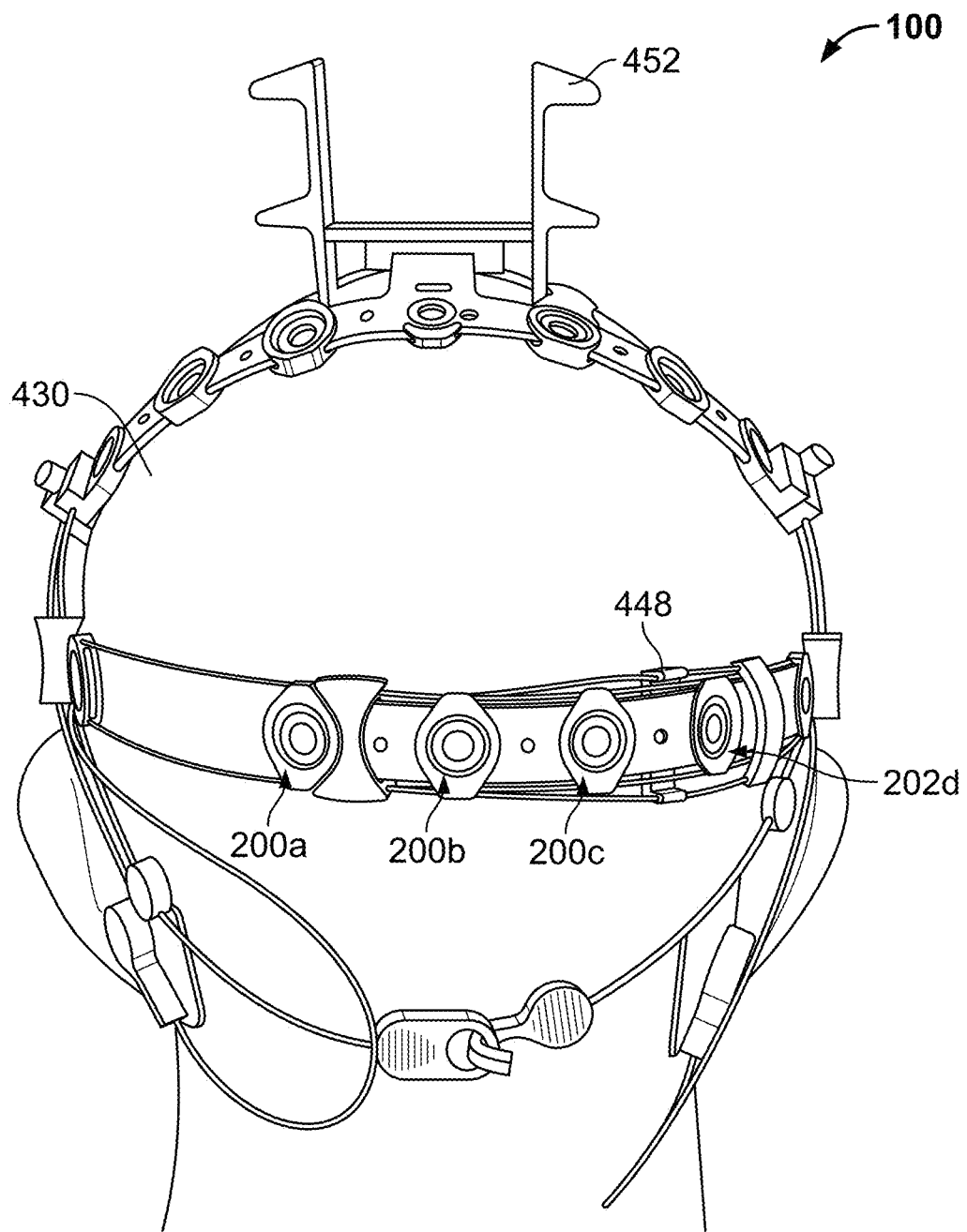
FIG. 4E is a rear view of the example headset of FIG. 1 disposed on a relatively large head.

When the headset 100 is used by a subject with a larger head, the rear of the head band 104 is disposed in a different location. For example, FIG. 4E shows the headset 100 on a larger head. As illustrated, the second aperture 200b is disposed along the midline of the head 430. Thus, in this configuration, the second aperture 200b may be used with an electrode to gather signals from the midline, and the first aperture 200a and the third aperture 200c may be used to gather left and right midline signals, respectively. Therefore, the example headset 100 can be used to obtain signals from the same three locations (a midline, a left and a right) when used on different sized heads.

In the illustrated example of FIGS. 4A-4E, supports 440a-440n are provided around the respective apertures 200a-200n. The supports 440a-440n provide support and centering for the electrodes that may be attached to and extend through the respective apertures 200a-200n. For example, as illustrated in FIG. 4D, a first support 440a is provided around first aperture 200a, a second support 440b is provided around the second aperture 200b, etc. In some examples, the supports 440a-440n are constructed of plastic.

To adjust the head band 104, the example headset 100 includes the lock 438. As illustrated in FIG. 4D, the lock 438 includes a release tab 442 that moves between a locked position and an unlocked position. In the illustrated example, the release tab 442 is in the locked position (to the left in FIG. 4D). The example headset 100 includes a first top wire 444a and a first lower wire 444b. As illustrated in FIGS. 4A and 4C, the first top and bottom wires 444a, 444b extend along the left side of the headset 100. The first top and bottom wires 444a, 444b are coupled to a fifth support 440e of a fifth electrode aperture 200e on the left side of the head band 104. The first top and bottom wires 444a, 444b extend rearward and pass through respective channels in a sixth support 440f and a seventh support 440g. Example channels are illustrated on the sixth support 440f in FIG. 4A (shown in dashed lines). Referring back to FIG. 4D, the first top and bottom wires 444a, 444b extend through channels in the first support 440a, through channels in the release tab 442, and through channels in the second support 440b. The first top and bottom wires 444a, 444b are coupled to a pull tab 446. The channels in the release tab 442 are offset from the channels in the first support 440a. As a result, when the release tab 442 is in the lock position (to the left and adjacent the first support 440a), the path for the first top and bottom wires 444a, 444b creates friction that prevents the first support 440a from sliding along the first top and bottom wires 444a, 444b. This is shown in the encircled area of FIG. 4D, which is an enlarged partial cross-sectional view of the first support 440a, the release tab 442 and the second support 440b showing example channels. In the illustrated example, the first support 440a includes a first channel 441 and the release tab 442 includes a second channel 443. The first channel 441 is slanted or angled with respect to the second channel 443, such that the first and second channels 441, 443 are not aligned when the first support 440a and the release tab 442 are adjacent each other. When the release tab 442 is in the locked position (to the left), the first top wire 444a is forced to bend through the channels 441, 443, which creates friction, thereby preventing the first support 440a from sliding along the first top wire 444a. Thus, the ends of the head band 104 are locked in place relative to each other. To release or adjust the head band 104, the release tab 442 is moved to the right (towards the second support 440b), which reduces or eliminates the friction. As a result, the first top and bottom wires 444a, 444b can slide freely through the first and second supports 440a, 400b and the release tab 442. The pull tab 446 can be pulled to the right to move the ends (the parts 302, 304 of FIG. 3) of the head band 104 toward each other, or can be moved back to the left to release the tensions and allow more space between the ends of the head band 104, as illustrated in FIG. 4E. The first top and bottom wires 444a, 444b increase the structural integrity of the head band 104. In some examples, the head band 104 is constructed of rubber (or another flexible material) and may tend to bend away from the head 430. In such an instance, the first top and bottom wires 444a, 444b hold or support the head band 104 in place. In some examples, the first top and bottom wires 444a, 444b are steel wires. In some examples, more than two wires may be implemented. In other examples, only one wire may be implemented instead of two. In some examples, the wire(s) may be coupled to other ones of the supports 440a-440n and/or to other locations on the head band 104. As illustrated in FIG. 4D, a spacer 448 is provided support the extra length of the first top and bottom wires 444a, 444b. The spacer 448 is movable along the head band 104. For example, as illustrated in FIG. 4E, the spacer 448 is moved further to the right.

As illustrated in FIG. 4B, the headset 100 includes a second top wire 450a and a second bottom wire 450b, which extend along the right side of the headset 100. The second top and bottom wires 450a, 450b are coupled to an eighth support 440h and extend rearward through channels in a ninth support 440i, a tenth support 440j, etc. Referring back to FIG. 4D, the second top and bottom wires 450a, 450b extend channels in the supports along the back of the head 440 and are coupled to the second support 440b. In some examples, the second top and bottom wires 450a, 450b also provide structural integrity to the head band 104. In some examples, more than two wires may be implemented. In some examples, the second top and bottom wires 450a, 450b are steel wires. In some examples, the wire(s) may be coupled to other ones of the supports 440a-440n and/or to other locations on the head band 104. In other examples, other tightening mechanisms and/or lock mechanisms may be implemented on the headset 100. In other examples, the head band 104 may be split or divided differently to dispose the lock 438 in other locations on the head 430 to ensure electrodes may be placed on areas desirable for EEG signal collection. In some examples, a processor support 452 (FIGS. 4D and 4E) is coupled to the headset 100 to support a processor (e.g., the processor 434 of FIG. 4C) when attached to the headset 100.

FIG. 5 shows an example electrode unit 500 that may be used with the example headset 100 of FIGS. 1-4E or another headset. The electrode unit 500 may be coupled to the first aperture 200a of FIGS. 2 and 3, for example. In some examples, multiple ones of the electrode unit 500 are used with the example headset 100 of FIGS. 1-4E.

In the illustrated example, the electrode unit 500 includes a pusher 502, a spring 504, a connector 506, a guide 508, a first electrode 510, a second electrode 512 and a housing 514. The guide 508 defines an opening 516. In the illustrated example, the first and second electrodes 510, 512 are slidably disposed within the opening 516 (e.g., a passage, a through-hole). The guide 508 is dimensioned to be disposed within an opening 518 in the connector 506. In some examples, the guide 508 is coupled to the connector 506 via an interference fit (e.g., friction or press fit). Additionally or alternatively, in some examples a chemical fastener such as an adhesive and/or a mechanical fastener(s) may be used to couple the guide 508 to the connector 506. In the illustrated example, the connector 506 is ring-shaped. The spring 504 is dimensioned to be disposed over the connector 506 and the guide 508. In the illustrated example, the spring 504 is a spiral spring plate. In an unbiased or relaxed position, the spring 504 is substantially flat or planar, as shown in the position in FIG. 5.

In the illustrated example, the guide 508 (with the first and second electrodes 510, 512), the connector 506 and the spring 504 are dimensioned to be disposed in a cavity 520 of the housing 514, such that the first and second electrodes 510, 512 extend from a bottom 522 of the housing 514. In the illustrated example, a first opening 521 in the housing 514 and a second opening 523 in the opposite side of the housing 514 define the cavity 520. The second spring 504 is disposed over the connector 506 and the guide 508 in the cavity 520. In some examples, the connector 506 is coupled to the housing 514 via an interference fit (e.g., friction or press fit). Additionally or alternatively, in some examples a chemical fastener such as an adhesive and/or a mechanical fastener(s) may be used to couple the connector 506 to the housing 514.

In the illustrated example, the electrodes 510, 512 are implemented as pins. However, in other examples, the electrodes may have other desired shapes such as, for example, rings, balls, hook-shaped, etc.

In the example of FIG. 6, the spring 504, the connector 506 (FIG. 5) and the guide 508 (FIG. 5) (with the first and second electrodes 510, 512) are disposed within the housing 514. As illustrated in FIGS. 5 and 6, the pusher 502 of this example includes a top 524 and a wall 526 extending from the top 524. As illustrated in FIG. 7, the pusher 502 of this example may be inserted into the cavity 520 (FIG. 5) of the housing 514 (through the second opening 523 (FIG. 5) of the housing 514). In particular, the wall 526 (FIGS. 5 and 6) is received within the cavity 520 (FIG. 5). The top 524 (FIGS. 5 and 6) includes a lip 527, the bottom surface of which engages a top 528 (FIG. 5) of the housing 514. In some examples, the pusher 502 is coupled to the housing 514 via an interference fit (e.g., friction or press fit). Additionally or alternatively, in some examples a chemical fastener such as an adhesive and/or a mechanical fastener(s) may be used to couple the pusher 502 to the housing 514.

Figure 8:
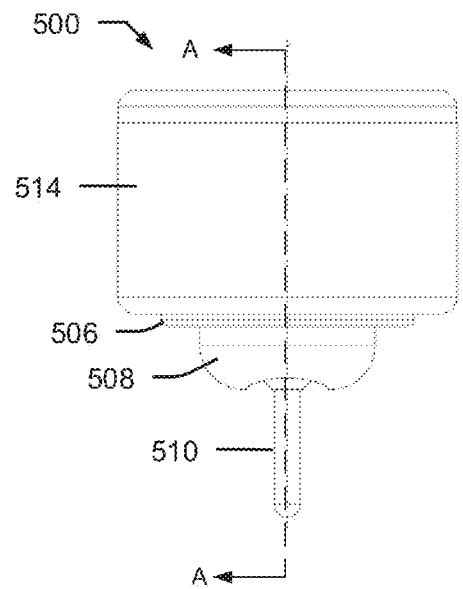
FIG. 8 is a side view of the example electrode unit of FIG. 5 with the example electrodes in an extended position.
Figure 9:
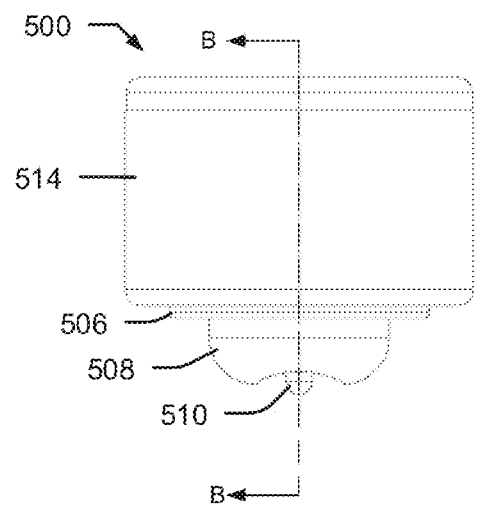
FIG. 9 is a side view of the example electrode unit of FIG. 5 with the example electrodes in a retracted or compressed position.
Figure 10:
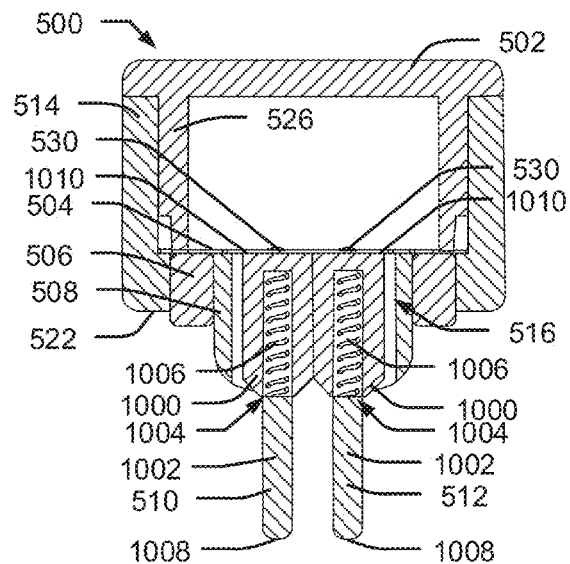
FIG. 10 is a cross-sectional view of the example electrode unit of FIG. 8 taken along line A-A of FIG. 8.
Figure 11:
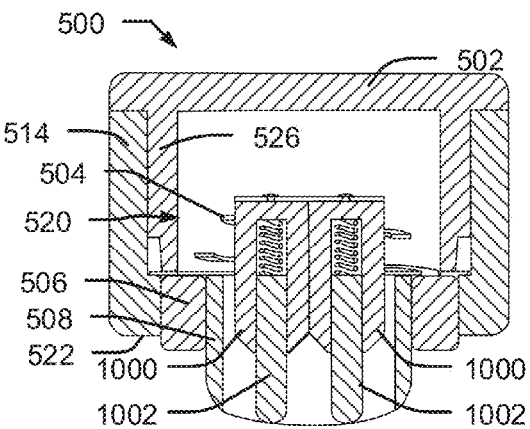
FIG. 11 is a cross-sectional view of the example electrode unit of FIG. 9 taken along line B-B of FIG. 9.

FIG. 8 is a side view of the example electrode unit 500 with the first and second electrodes 510, 512 (FIG. 5) in the extended position, and FIG. 9 is a side view of the example electrode unit 500 with the first and second electrodes 510, 512 (FIG. 5) in the retracted position. FIG. 10 is a cross-sectional view of the electrode unit 500 of FIG. 8 taken along line A-A of FIG. 8, and FIG. 11 is a cross-sectional view of the electrode unit 500 of FIG. 11 taken along line B-B of FIG. 9. As illustrated in FIGS. 8-11, the guide 508 is received within the connector 506, and the connector 506 is received within the cavity 520 of the housing 514. The connector 506 is substantially aligned with the bottom 522 (FIGS. 10 and 11) of the housing 514, and the guide 508 and the first and second electrodes 510, 512 extend from the bottom 522 of the housing 514.

As shown in the illustrated example of FIGS. 10 and 11, the first electrode 510 includes a first electrode body 1000 (e.g., a housing, a sheath) and a first pin 1002 (e.g., a pogo pin). The first electrode body 1000 receives the first pin 1002 within a first cavity 1004 of the first electrode body 1000. The first pin 1002 of the illustrated example is retractable into the first cavity 1004 and biased outward from the first electrode body 1000 (e.g., from an end of the first electrode body 1000) by a first spring 1006 that is disposed within the first cavity 1004. A tip 1008 of the first pin 1002 contacts the scalp of the head of a subject and senses the EEG signals. The first spring 1006 allows the first pin 1002 to retract into the first electrode body 1000 when force is applied downward against the scalp and, thus, increases the comfort and wearability of the headset (e.g., the headset 100 of FIG. 1) by reducing the pressure the first electrode 510 applies to the scalp. In some examples, to prevent the first pin 1002 from being inadvertently removed from the first electrode body 1000, the first pin 1002 is coupled (e.g., via welding) to one end of the first spring 1006, and the other end of the first spring 1006 is coupled to the first electrode body 1000. Additionally or alternatively, the first pin 1002 may include a leg or lip that abuts a rim around the inside of the first cavity 1004. The leg or lip may be forced passed the rim (e.g., via a snap fit) when first inserting the first pin 1002 into the first cavity 1004. In other examples, a chemical fastener such as an adhesive and/or a mechanical fastener(s) may be used prevent the first pin 1002 from being completely ejected from the first electrode body 1000. Different size springs or springs of different material may be utilized with the first electrode 510 to provide more or less biasing force. In some examples, the first spring 1006 provides around 0.2 Newtons of force. In the illustrated example, the first spring 1006 is a coil spring. In other examples, the first spring 1006 may be implemented by any other type of spring such as, for example, a leaf spring.

In the illustrated example of FIGS. 10 and 11, the second electrode 512 is substantially the same as (e.g., identical to) the first electrode 510. In particular, the second electrode 512 includes a second electrode body 1000, a second pin 1002, a second cavity 1004, a second spring 1006 and a second tip 1008. As such, the second electrode 512 operates substantially the same as the first electrode 510. Thus, to reduce redundancy, the second electrode 512 will not be further described herein. Instead, the interested reader is referred to the disclosure above relating to the first electrode 510 for a complete description of the second electrode 512.

In the extended position of the pins 1002 illustrated in FIGS. 8 and 10, the spring 504 (FIG. 10) is substantially flat, and the ends of the first electrode body 1000 of the first electrode 510 and the second electrode body 1000 of the second electrode 512 are disposed flush with the opening 516 of the guide 508 (see FIG. 10). In addition, the first pin 1002 of the first electrode 510 extends from the first cavity 1004 (e.g., from a first end) of the first electrode body 1000, and the second pin 1002 of the second electrode 512 extends from the second cavity 1004 of the second electrode body 1000. A first top 1010 (e.g., a second end) of the first electrode body 1000 engages the spring 504, and a second top 1010 of the second electrode body 1000 engages the spring 504. The second spring 504 is disposed over the opening 516 adjacent the first top 1010 and the second top 1010 of the first and second electrodes 510, 512. In some examples, the first top 1010 and/or the second top 1010 are coupled to the spring 504. In the illustrated example, the outer rim/perimeter of the spring 504 is coupled (e.g., retained) between the wall 526 of the pusher 502 and the connector 506, which are coupled to the housing 514 (e.g., via an interference fit). In some examples, the pusher 502 provides force to keep the spring 504 in contact with the connector 506 (e.g., for communicating EEG signals therethrough). In some examples, the pusher 502 covers the internal components of the electrode unit 500 to prevent accidently damage and/or contact with the spring 504.

In some examples, the first electrode 510 is coupled (e.g., fixedly coupled) to the spring 504 via staking or press fit. For example, the first electrode 510 includes a first protrusion 530 (e.g., a boss) (as shown in FIGS. 5 and 10) extending from the first top 1010 of the first electrode body 1000. As illustrated in FIG. 5, the spring 504 includes a first aperture 532 (e.g., a hole). The first protrusion 530 is inserted into the first aperture 532 and flattened or deformed (e.g., via a staking punch, or heat) to fasten the first electrode 510 to the spring 504. Similarly, the second electrode 512 includes a second protrusion 530 (e.g., a boss) (as shown in FIGS. 5 and 10) extending from the second top 1010 of the second electrode body 1000, and the spring 504 includes a second aperture 536 through which the second protrusion 530 can be inserted and fastened (e.g., via deformation). Additionally or alternatively, in some examples other mechanical and/or chemical fastener(s) may be used to couple the first electrode 510 and/or the second electrode 512 to the spring 504. For example, the first electrode 510 and/or the second electrode 512 may be soldered to the spring 504. In the illustrated example, the first electrode 510 and the second electrode 512 are independently adjustable via the respective springs 1006.

In the retracted position of the electrode pins 1002 illustrated in FIGS. 9 and 11, the first and second electrodes 510, 512 have been forced through the opening 516 in the guide 508 and into the spring 504 such that the tops 1010 are disposed above the opening 516 and further within the guide 508 (see FIG. 11). In other words, the first and second electrodes 510, 512 are movable through the opening 516 of the guide 508 into the cavity 520 of the housing 514. The spring 504 flexes to enable this movement of the first and second electrodes 510, 512 to the retracted position. In particular, when the first and second electrodes 510, 512 move into the cavity 520 of the housing 514, a center of the spring 504 flexes into the cavity 520. As the center of the spring 504 flexes, the outer rim of the spring 504 remains in contact with the connector 506. The spring 504, thus, further softens the force of the pins 1002 against the scalp and increases comfort to the subject wearing the headset 100 because the spring 504 enables the first and second electrodes 510, 512 to retract into the housing 514 and the pusher 502 when a sufficient force is applied by, for example, a tightening of the headset 100. By comparing FIGS. 10 and 11, it can be seen that, in addition to the extension of the spring 504, the springs 1006 within the individual electrodes 510, 512 compress when subjected to force. Thus, the spring 504 and the springs 1006 provide an additive force on the scalp. The springs 1006 in the electrodes 510, 512 enable the electrode pins 1002 to independently adjust to bumps and curves on the scalp. Thus, the first pin 1002 has been retracted into the first electrode body 1000 and the second pin 1002 has been retracted into the second electrode body 1000, which further softens the force against the scalp and increases comfort. Without the spring 504, retraction of the electrode pins 1002 would be limited by the first electrode body 1000 and second electrode body 1000, respectively, and any additional application of force would be transmitted from the first pin 1002 and second pin 1002 into the scalp of the subject wearing the headset 100. Because the first electrode body 1000 and the second electrode body 1000 are independently movable, depending on the placement of the electrodes, the curvature of the scalp, an amount of hair, and/or a degree to which the bands are tightened or loosened, the first electrode body 1000 may extend a first distance from the guide 508, and the second electrode body 1000 may extend a second distance from the guide 508. In some examples, the second distance is different than the first. In some examples, the first electrode 510 and second electrode 512 are simultaneously adjustable via the spring 504 and independently adjusted via the springs 1006.

In the illustrated example, the connector 506 is magnetic. As such, the electrode unit 500 may be magnetically coupled to the body 102. For example, the first connector 202*a* of FIG. 3 is a magnetic ring and the connector 506 (FIGS. 5, 10 and 11) is a magnetic ring. Thus, for example, when the electrode unit 500 is placed on the first aperture 200*a*, the first connector 202*a* and the connector 506 magnetically couple the electrode unit 500 to the body 102. In the illustrated example, bottom of the guide 508 extends into the first aperture 200*a*, and the first and second electrodes 510, 512 extend through the first aperture 200*a* and outward from the bottom of the body 102. In other examples, the connectors 202*a*, 506 may be other types of connectors. These magnetic couplings (or other releasable mechanical couplings) allow the electrode units 500 to be independently coupled to the headset 100. As such, the independently couplable electrode units 500 can be repaired or replaced individually, which extends the useful life of the headset 100 by enabling replacement of individual electrode units 500 instead of the entire headset 100.

The first and second electrodes 510, 512 sense EEG signals from the scalp of a subject. The signals are transferred from the pins 1002 through the electrode bodies 1000, the spring 504, and the connector 506 to the first connector 202*a*. As described above, a PCB may be disposed within the body 102 to electrically couple the first connector 202*a* to the processor 434 (FIG. 4C) and/or a transmitter. In some examples, the first and second electrodes 510, 512 and the spring 504 are electrically conductive, whereas the guide 508 and the housing 514 are not electrically conductive. For example the first and second electrodes 510, 512 and the spring 504 may be metallic (e.g., steel, silver, silver-chloride, chromium, gold, etc.) and the guide 508 and the housing 514 may be plastic or rubber and/or other suitable material(s) or combination of material(s).

In the illustrated example, the electrode unit 500 includes two electrodes. However, in other examples, the electrode unit 500 may include more or fewer electrodes and/or pins. For example, the electrode unit 500 may include only one electrode. In another example, the electrode unit 500 may include three electrodes, four electrodes, ten electrodes, etc.

Figure 12:
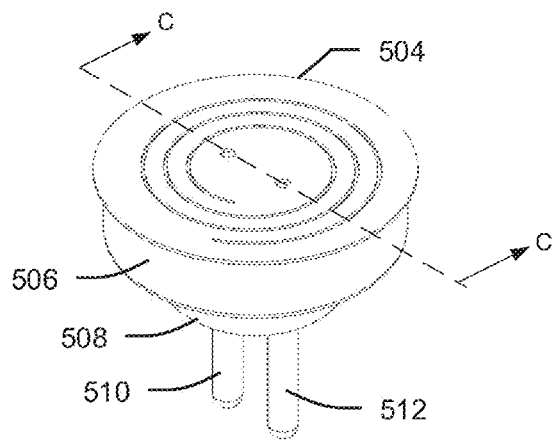
FIG. 12 is a perspective view of the example electrode unit of FIG. 5 with the example electrodes in an extended position.
Figure 13:
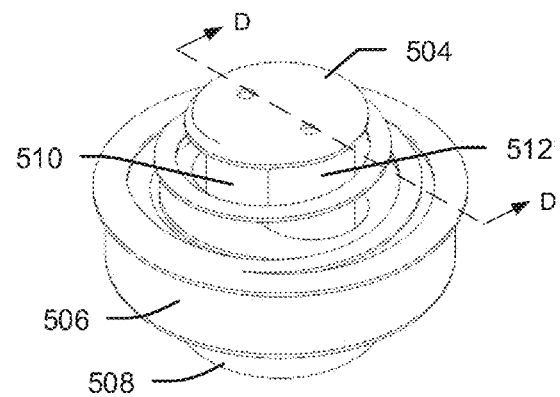
FIG. 13 is a perspective view of the example electrode unit of FIG. 5 with the example electrodes in a retracted position.

FIG. 12 shows the spring 504, the connector 506, the guide 508 and the first and second electrodes 510, 512 of the electrode unit 500 (FIG. 5) in the extended position, similar to FIGS. 8 and 10. In FIG. 12, the pusher 502 and the housing 514 have been removed for clarity. In the illustrated example, the spring 504 is relaxed or in an unbiased state. FIG. 13 shows the spring 504 in a biased state, similar to FIG. 11. The first and second electrodes 510, 512 (FIG. 12) are pushed upward through the guide 508 and onto the bottom of the spring 504. As a result, a middle of the spring 504 flexes upward. In the biased state, the spring 504 biases the first and second electrodes 510, 512 downward.

Figure 14:
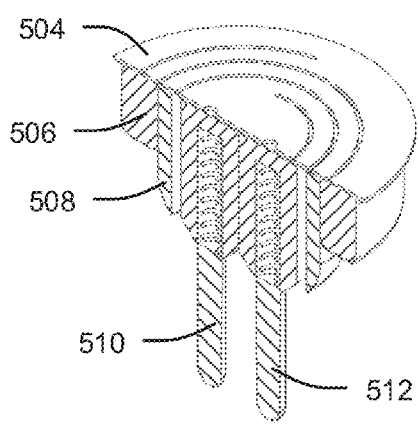
FIG. 14 is a cross-sectional view of the example electrode unit of FIG. 12 taken along line C-C of FIG. 12.
Figure 15:
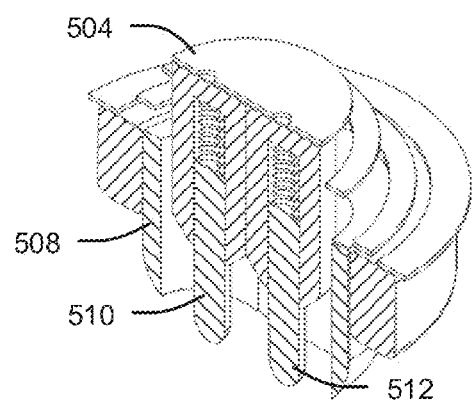
FIG. 15 is a cross-sectional view of the example electrode unit of the FIG. 13 taken along line D-D of FIG. 13.

FIG. 14 is a cross-sectional view of the spring 504, the connector 506, the guide 508 and the first and second electrodes 510, 512 taken along line C-C of FIG. 12, showing the first and second electrodes 510, 512 in the extended position, similar to FIG. 10. FIG. 15 is a cross-sectional view of the spring 504, the connector 506, the guide 508 and the first and second electrodes 510, 512 taken along line D-D of FIG. 13, showing the first and second electrodes in the retracted position, similar to FIG. 11.

FIGS. 16-18 illustrate another example electrode unit 1600 that may be used with the example headset 100 of FIGS. 1-4E. In FIGS. 16-18, the electrode unit 1600 is illustrated as coupled to the head band 104 of the headset 100 (FIG. 1). In the illustrated example, the electrode unit 1600 includes an electrode 1602, a housing 1604, a connector 1606 and insulation 1608. As illustrated in FIG. 18, the electrode 1602 includes an electrode body 1610 (e.g., a housing, a sheath) and a pin 1612 (e.g., a pogo pin). The electrode body 1610 receives the pin 1612 within a cavity 1614 of the electrode body 1610. The pin 1612 of the illustrated example is retractable into the cavity 1614 and biased outward from the electrode body 1610 by a spring 1616 that is disposed within the cavity 1614. A tip 1618 of the pin 1612 contacts the scalp of the head of a subject and senses the EEG signals.

In the illustrated example of FIGS. 16-18, the insulation 1608 and the electrode body 1610 are disposed within a cavity 1620 of the housing 1604. The insulation 1608 is located between the electrode body 1610 and an inner wall 1622 of the cavity 1620. In some examples, the cavity 1620 is implemented as a blind hole.

As discussed above, the bands 104, 106, 108, 110, 112 of the headset 100 include the plurality of apertures 200*a*-200*n* extending through the bands 104, 106, 108, 110, 112, and the plurality of connectors 202*a*-202*n* are disposed around the apertures 200*a*-200*n*. In FIGS. 16-18, the electrode unit 1600 is illustrated as coupled to the first aperture 200*a*. The electrode 1602 extends through the first aperture 200*a*. In the illustrated example, the connector 1606 is a magnet, and the first connector 202*a* is a metal ring. As such, the electrode unit 1600 is magnetically coupled to the head band 104, and, thus, releasably coupled thereto. In the illustrated example, the connector 1606 is disposed between a flange 1623 extending from the electrode body 1610 and the insulation 1608. When the electrode unit 1600 is disposed on the head band 104, the attractive force between the connector 1606 and the first connector 202*a* retains in the electrode unit 1600 on the head band 104. In other examples, the connector 1606 and the first connector 202*a* may be other types of connectors to removably couple the electrode unit 1600 to the head band 104.

As illustrated in FIGS. 16 and 18, a PCB 1624 is disposed within (e.g., entirely encased in) the head band 104. The PCB 1624 communicatively couples the first connector 202*a* to the electrical connector 300 (FIG. 4C). Signals gathered by the electrode 1602 are transferred from the electrode pin 1612, through the electrode body 1610 and the flange 1623, to the first connector 202*a*, to the PCB 1624 and, thus, to the electrical connector 300. Because the PCB 1624 acts primarily as a conductor and need not include logic circuitry, in some examples the PCB 1624 is replaced with other conductors such as wires.

In some examples, shielding is desired to block or prevent noise or other signals (e.g., interference) from adversely affecting the EEG signals gathered by the electrode 1602. In the illustrated example, the head band 104 includes an electrical pin 1626 adjacent the first aperture 200*a*. When the electrode unit 1600 is coupled to the first aperture 200*a*, the electrical pin 1626 contacts a bottom 1628 of the housing 1604. A layer of conductive paint or paste 1630 is disposed on the bottom 1628 of the housing and along the inner wall 1622 of the cavity 1620. The electrical pin 1626 is coupled (e.g., soldered) to the PCB 1624. In some examples, a wire or trace in the PCB 1624 electrically couples the pin 1626 to a shielding electrode, which may be in contact with the head (e.g., forehead) of the subject. Thus, the paste 1630 is in electrical connection with the body of the wearer, which acts as an extension of the body that surrounds the electrode 1602, thereby shielding the electrode 1602 from any interference or noise in the environment. For example, referring back to FIG. 2, the example headset 100 includes six flat electrodes 204a, 204b, 204c, 204d, 204e, 204f coupled to the head band 104 (e.g., molded in the body 102 of the head band 104) and disposed along the forehead side of the head band 104. The flat electrodes 204a-204f are communicatively coupled to the PCB 1624 in the body 102 of the headset 100 and/or to other wires or traces disposed in the body 102 of the headset 100. In some examples, one of the flat electrodes 204a-204f is a shielding electrode, which is communicatively coupled to the pin 1626 (and other pins associated with the other apertures 200a-200n). In some examples, three of the flat electrodes 204a-204f are to gather EEG signals, one of the flat electrodes 204a-204f is a ground electrode, one of the flat electrodes 204a-204f is a reference or feed-back electrode and one of the flat electrodes 204a-204f is a shielding electrode. In other examples, one or more of the flat electrodes 204a-204f may have different functions. In some examples, more or fewer flat electrodes are implemented.

In some examples, a shield layer (e.g., a layer of silver or copper) is disposed on top of the PCB 1624 (or molded into the body 102 of the headset 100 over the PCB 1624) and integrated throughout the body 102 of the headset 100. The shield layer is also electrically coupled to the shielding electrode on the forehead of the subject and, thus, shields the PCB 1624 in a similar manner. In some examples, the shield layer is electrically coupled to a shield layer in the processor 434 (which is disposed over the electrical components in the processor 434) to likewise shield any electrical components in the processor 434. Thus, a passive shield can be formed around the electrical components of the headset 100. In other examples, a charge may be provided to the pin 1626 and are distributed throughout the paste 1630 to block noise and interference. In some examples, a metallic mesh or pattern (e.g., a cage) is disposed around the electrode 1602. In some examples, the electrical pin 1626 is biased upward from the head band 104 (e.g., via a spring, similar to the first spring 1006 and the first pin 1002 in FIG. 10) such that the electrical pin 1626 retracts into a base or body when contacted by the housing 1604. In other examples, the electrical pin 1626 is integrated with the electrode unit 1600 and contacts a pad near the first aperture 200a when connected to the headset 100 (disclosed in further detail here).

In FIGS. 16-18, the electrode unit 1600 is illustrated as coupled to the head band 104. However, in other examples, the electrode unit 1600 may be similarly coupled to other ones of the bands (e.g., the first band 106, the second band 108, the third band 110, or the midline band 112). In some examples, multiples electrode units similar (e.g., identical) to the electrode unit 1600 are coupled to the headset 100 (FIGS. 1-4E).

FIGS. 19, 20 and 21 illustrate another example electrode unit 1900 that may be used with the example headset 100 of FIGS. 1-4E. In the illustrated example, the electrode unit 1900 includes an electrode 1902, a housing 1904 and a connector 1906. In FIGS. 19 and 20, the interior structure of the housing 1904 is shown in dashed lines. The electrode 1902 includes an arm 1908 and a ring 1910. In the illustrated example, the housing 1904 includes a cavity 1912. The ring 1910 of the electrode 1902 is disposed around an opening 1914 of the cavity 1912. In the illustrated example, the ring 1910 is coupled between the connector 1906 and a bottom 1916 of the housing 1904. The arm 1908 is bent or curved in this example. A first end of the arm 1908 is coupled to the ring 1910, and the other end of the arm 1908 extends through an opening 1918 of the ring 1910 and into the cavity 1912 of the housing 1904 (see also FIG. 25).

The example electrode unit 1900 may be coupled to one of the apertures 200a-200n of the headset 100 of FIGS. 1-4. In some examples, the connector 1906 is a magnet, and the connectors 202a-202n (FIG. 3) are metal rings. As such, the connector 1906 magnetically couples the electrode unit 1900 to one of the connectors 202a-202n. When coupled to one of the connectors 202a-202n, the arm 1908 of the electrode 1902 extends through the respective aperture 200a-200n to contact the scalp of a subject when the headset 100 is disposed on the head of the subject. In FIGS. 19-21, the example electrode 1902 is in an uncompressed state. Signals gathered by the electrode 1902 are transferred through the connector 1906 to the connector 202a-202n and to the electrical connector 300 (FIG. 3) via the PCB (or other connective wiring) disposed within the body 102 of the headset 100.

FIGS. 22-24 illustrate the example electrode 1902 in an unassembled (e.g., unshaped or unbent) state or form. The electrode 1902 may be stamped or cut from a substrate such as, for example, a sheet of silver, silver-chloride, chromium, gold, and/or any other suitable metal(s), alloy(s) or other conductive material(s) or combination thereof. In the illustrated example, the electrode 1902 includes the ring 1910 and the arm 1908 extending from the ring 1910. FIGS. 25-27 illustrate the electrode 1902 in an assembled state or form. To form the electrode 1902 from the unassembled electrode 1902 of FIG. 22, the arm 1908 is bent over the ring 1910, inserted through the opening 1918 and creased or bent, such that a portion of the arm 1908 extends back through the opening 1918. For example, as illustrated in FIGS. 25-27, a first portion 2500 of the arm 1908 extends downward from the ring 1910 (through the opening 1918) and, at a corner or bend 2502, a second portion 2504 of the arm 1908 extends back upward through the opening 1918 of the ring 1910. The first and second portions 2500, 2504 are coupled at the bend 2502. In some examples, the first and second portions 2500, 2504 are integral. The electrode 1902 as illustrated in FIG. 25 may be formed by bending the arm 1908 over the ring 1910 and through the opening 1918. In other examples, the arm 1908 may be bent downward on the outside of the circumference of the ring 1910, bent or creased to form the corner or bend 2502 and positioned back through the opening 1918 of the ring 1910. Other examples include a curve in place of the bend 2502, which may be used, for example, to increase the surface area of the connection of the electrode 1902 on the scalp and/or provide increased comfort to the subject.

FIGS. 28-30 illustrate the example housing 1904 of the electrode unit 1900 (FIG. 19). In particular, FIG. 28 is a side view of the housing 1904, FIG. 29 is a bottom view of the housing 1904 and FIG. 30 is a cross-sectional view of the housing 1904 taken along line G-G of FIG. 28. As illustrated in FIGS. 29 and 30, the cavity 1912 extends into the housing 1904 from the opening 1914 in the bottom 1916. In the illustrated example, a first groove or recess 2900 is formed around the opening 1914. The first recess 2900 is sized to receive the connector 1906 (FIG. 19). A second groove or recess 2902 is formed above the first recess 2900 and is sized to receive the ring 1910 (FIG. 19) of the electrode 1902. In some examples, the connector 1906 is retained in the first recess 2900 via an interference fit (e.g., friction fit). In other examples, chemical, magnetic, and/or mechanical fasteners may be used to couple to the connector 1906 to the housing 1904.

In the illustrated example, the cavity 1912 includes a first channel 2904 (e.g., a slot) and a second channel 2906 extending into the housing 1904. When the arm 1908 of the electrode is compressed, the second portion 2504 (FIG. 25) of the arm 1908 is disposed within one of the first channel 2904 or the second channel 2906 (as discussed in further detail herein). As such, the electrode 1902 can be oriented in one of two orientations (e.g., with the second portion 2504 extending into the first channel 2904 or the second channel 2906). In other examples, the cavity 1912 may include only one channel. In other examples, the cavity 1912 may include more than two channels, or may include a continuous channel such that electrode 1902 can be positioned in the housing 1904 in any orientation.

In the illustrated example of FIGS. 29 and 30, a guide 2908 is disposed within the cavity 1912. The guide 2908 is a cylinder that extends from an inner wall of the cavity 1912 and is sized to receive the ring 1910 of the electrode 1902 and align the electrode 1902 within the opening 1914 of the housing 1904. As illustrated in FIG. 29, the guide 2908 includes a first slot 2910 that is aligned with the first channel 2904 of the cavity 1912 and a second slot 2912 that is aligned with the second channel 2906 of the cavity 1912. As a result, the arm 1908 of the electrode 1902 can extend through one of the first or second slots 2910, 2912 and into the respective first or second channel 2904, 2906 of the cavity 1912.

FIGS. 31-33 illustrate the example electrode 1902 of the electrode unit 1900 in a bent or compressed state, such as when the electrode 1902 is in contact with the scalp of a subject. In FIGS. 31 and 32, the interior structure of the housing 1904 is shown in dashed lines. For example, when the electrode unit 1900 is attached to a headset (e.g., the headset 100 of FIGS. 1-4), the electrode 1902 extends through an aperture in the headset to contact the head of a subject. In particular, the bend 2502 contacts the head of the subject. The arm 1908 bends or compresses to reduce or soften the contact between the bend 2502 and the scalp of the subject. In other words, the electrode 1902 acts as a spring to biases the bend 2502 downward from the opening 1914. The electrode 1902 has a similar mechanical movement as a leaf spring. As illustrated in FIGS. 31-33, when a force is applied to the bend 2502 (e.g., resistance from the scalp of the subject when the headset 100 is tightened), the first portion 2500 and the second portion 2504 of the arm 1908 bend or curve. In some examples, the first portion 2500 moves toward the second portion 2504 when force is applied to the bend 2502. As the bend 2502 is moved upward toward the opening 1914, the second portion 2504 of the arm 1908 slides into the first channel 2904 of the cavity 1912. Referring back to FIGS. 22, 23, and 25, the ring 1910 includes a notch 2506 formed in the rim of the opening 1918. In some examples, when the arm 1908 is compressed, as illustrated in FIGS. 31-33, the second portion 2504 is moved into the notch 2506, and the notch 2506 functions as a guide. EEG signals are transferred from the bend 2502, through the first portion 2500 (or the second portion 2504) to the ring 1910, to the connector 1906, and from the connector 1906 to one of the connectors 202a-202n (FIG. 3) of the headset 100.

The signals are then transferred from the one of the connectors 202a-202n to the electrical connector 300 (FIG. 4A) via the PCB.

Figure 34:
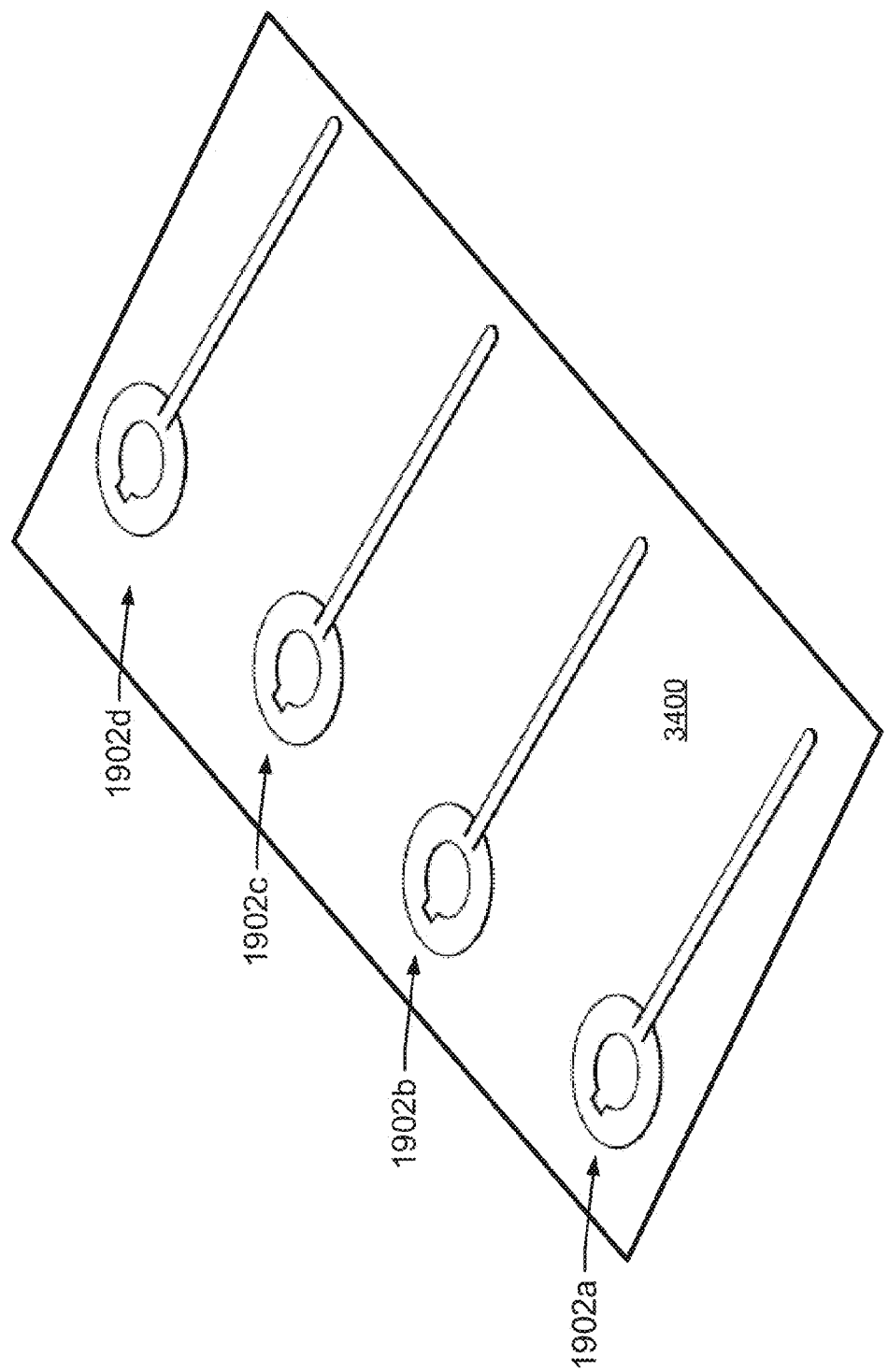
FIG. 34 illustrates an example substrate from which multiple ones of the example electrode of FIG. 19 are stamped during an example manufacturing process.

As disclosed herein, the electrode 1902 may be stamped or cut from a substrate such as, for example, the substrates disclose above. FIG. 34 illustrates example electrodes 1902a-1904d stamped into a substrate 3400. The substrate 3400 may include steel, silver, silver-chloride, chromium, gold and/or any other suitable material or combination of material(s). As such, multiple electrodes can be manufactured relatively quickly and for low cost.

FIGS. 35-39 illustrate another example electrode unit 3500 that may be used with the example headset 100 of FIGS. 1-4E. As illustrated in the exploded view of FIG. 35, the electrode unit 3500 includes a housing 3502, a spring 3504, a support 3506, a first electrode 3508, a second electrode 3510, a guide 3512 and a connector 3514. In the illustrated example, the first and second electrodes 3508, 3510 are substantially the same as the first and second electrodes 510, 512 of the electrode unit 500 (FIG. 5) and include pins (e.g., pogo pins) that are biased outward. In the illustrated example, the first and second electrodes 3508, 3510 are coupled to the spring 3504 via the support 3506. In some examples, the support 3506 includes one or more tabs or protrusions that extend through openings in the spring 3504 and which may be staked or press fit (similar to the first and second electrodes 510, 512). In other examples, the support 3506 is coupled to the spring 3504 via other mechanical and/or chemical fasteners.

The first and second electrodes 3508, 3510 are slidably disposed within an opening 3516 of the guide 3512, and the guide 3512 is dimensioned to be disposed within an opening 3518 of the connector 3514. In some examples, the guide 3512 is coupled to the connector 3514 via an interference fit (e.g., friction or press fit). Additionally or alternatively, in some examples a chemical fastener such as an adhesive and/or a mechanical fastener(s) may be used to couple the guide 3512 to the connector 3514. The connector 3514 is dimensioned to be inserted into an opening 3520 in the housing 3502. In some examples, the connector 3514 is coupled to the housing 3502 via an interference fit (e.g., friction or press fit). Additionally or alternatively, in some examples a chemical fastener such as an adhesive and/or a mechanical fastener(s) may be used to couple the connector 3514 to the housing 3502. When the connector 3514 is inserted into the opening 3520 of the housing 3502, the spring 3504 is clamped between the connector 3514 and a ledge 3522 in the opening 3520 of the housing 3502. The connector 3514 couples the electrode unit 3500 to one of the connectors 202a-202n of the example headset 100 in FIGS. 1-4E, similar to the other electrode units disclosed herein. When the electrode unit 3500 is assembled, the spring 3504 is disposed over the opening 3516 of the guide 3512. Similar to the electrode unit 500 (FIG. 5) disclosed above, the spring 3504 increases the comfort and wearability of the headset 100 by reducing the pressure the first and second electrodes 3508, 3510 apply to the scalp. As the first and second electrodes 3508, 3510 are pushed upwards, the center section of the spring 3504 flexes upward into the opening 3520 of the housing 3502. Electrical signals from the first and second electrodes 3508, 3510 are transmitted through the support 3506 to the spring 3504, and through the spring 3504 to the connector 3514, which is in contact with one of the connectors 202a-202n of the headset 100 (FIGS. 1-4E).

FIG. 36 illustrates an assembled view of the example electrode unit 3500, FIG. 37 illustrates a side view of the example electrode unit 3500, FIG. 38 illustrates another side view of the example electrode unit 3500, and FIG. 39 illustrates a cross-sectional view of the example electrode unit 3500 taken along line I-I of FIG. 38. As illustrated in FIGS. 36-39, when the connector 3514 is received within the housing 3502, the connector 3514 is substantially flush or even with a bottom 3524 of the housing 3502 and the guide 3512 and the first and second electrodes 3508, 3510 extend from the bottom 3524 of the housing 35012. When the first and second electrodes 3508, 3510 contact the scalp, the pins of the first and second electrodes 3508, 3510 retract and/or the first and second electrodes 3508, 3510 retract into the opening 3520 of the housing 3502 as disclosed in other examples herein. As illustrated in FIG. 39, the outer rim/perimeter of the spring 3504 is coupled (e.g., retained) between ledge 3522 of the housing 3502 and the connector 3514, which is coupled to the housing 3502.

In some examples, shielding may be desired for the electrode unit 3500. FIG. 40 illustrates an example shielding unit 4000 that may be implemented to shield the example electrode unit 3500. In the illustrated example, the shielding unit 4000 includes a top cover 4002 (e.g., a first cover) and a bottom cover 4004 (e.g., a second cover). The bottom cover 4004 includes an opening 4006 to receive the electrode unit 3500. The opening 4006 extends from a top side 4007 to a bottom side 4009 of the bottom cover 4004. When the electrode unit 3500 is disposed in the bottom cover 4004, the first and second electrodes 3508, 3510 extend from the bottom, such that the first and second electrodes 3508, 3510 can extend through one of the apertures 200a-200n of the example headset 100 (FIGS. 1-4E). For example, in the illustrated example, the shielding unit 4000 (with the electrode unit 3500 disposed therein) may be coupled to the first aperture 200a on the head band 104. The connector 3514 couples (e.g., magnetically) the electrode unit 3500 (and, thus, the shielding unit 4000) to the connector 202a. The top cover 4002 is coupled to the top side 4007 of the bottom cover 4004.

In some examples, to retain the electrode unit 3500 in the bottom cover 4004, the housing 3502 is coupled to the bottom cover 4004 via an interference fit (e.g., friction or press fit). Additionally or alternatively, in some examples a chemical fastener such as an adhesive and/or a mechanical fastener(s) may be used to couple the housing 3502 to the bottom cover 4004. In the illustrated example, the shielding unit 4000 includes a pin 4008 that is disposed within a channel 4010 extending through the bottom cover 4004. The pin 4008 extends from the bottom cover 4004 and, when the shielding unit 4000 is coupled to one of the apertures 200a-200j of the headset 100, the pin 4008 contacts an electrical pad 4012 (e.g., a metal pad) adjacent the first aperture 200a. The other end of the pin 4008 contacts a layer of conductive paste 4014 that is distributed around a bottom 4016 of the top cover 4002, similar to the layer of conductive paste 1630 on the bottom 1628 of the housing 1604 in FIG. 18. In some examples, the pin 4008 is a pogo-pin (e.g., similar to the pogo-pin electrode in FIG. 41). The electrical pad 4012 is electrically coupled, via the PCB 1624 and/or other traces or wires, to a shield electrode (e.g., one of the flat electrodes 204a-204f (FIG. 2) the forehead), similar to the example electrode unit 1600 in FIGS. 16-19. In the illustrated example, the pin 4008 is a spring-loaded pin (e.g., a pogo-pin), similar to the pin 1626 of FIGS. 16-18. In other examples, the pin 4008 is not spring-loaded. While the example shielding unit 4000 is described in connection with the example electrode unit 3500, it is understood that any other electrode unit such as the example electrode units 500, 1600, 1900 may be similarly contained in the shielding unit 4000. As such, the example shielding unit 4000 can be employed to provide shielding to other electrode units.

Figure 41:
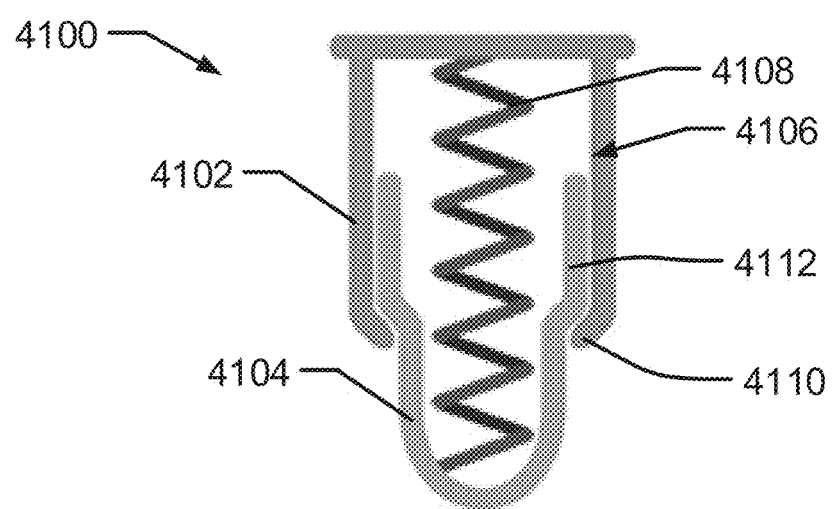
FIG. 41 is a cross-sectional view of an example pogo-pin electrode that may be implemented as any of the example electrodes disclosed herein.

FIG. 41 illustrates a cross-sectional view an example pogo-pin electrode 4100. Any of the example electrodes disclosed herein (e.g., the electrodes 510, 512, 1602, 3508, 3510) may be implemented as the example electrode 4100. The electrode 4100 includes a body 4102 and a pin 4104 that is retractable into an opening 4106 in the body 4102. A spring 4108 is disposed in the opening 4106 and biases the pin 4104 outward. To keep the pin 4104 from being ejected from the opening 4106, an edge 4110 of the body 4102 around the opening 4106 is angled inwards. Additionally, an upper section 4112 of the pin 4104 is widen. The upper section 4112 of the pin 4104 engages the edge 4110 of the body 4102, which prevents the pin 4104 from being ejected.

In some examples, one or more ground electrodes are implemented in gathering the EEG signals. A ground electrode may be coupled to another part of the subject's body, such as the ear, the finger, the forehead (e.g., one of the flat electrodes 204a-204f of FIG. 2), behind the mastoid, etc. The ground electrode(s) are electrically coupled to a signal acquisition unit (e.g., the processor 434 of FIG. 4C). In some examples, one or more body-sense electrodes (e.g., a control electrode, a reference electrode, a feed-back electrode) are used to enhance the signal acquisition process. The body-sense electrode(s) are coupled to the ear lobe, the nose, and/or any other area on the body having sufficient connectivity and low exposure to brain and/other body signals. The body sense electrode may be one of the flat electrodes 204a-204f of FIG. 2, for example. The body sense electrode (s) measure or obtain signals generated by noise and interference in the environment. The noise or interference signals can be subtracted from the desired signals obtained by the electrodes on the headset, thereby offsetting any noise or interface signals picked up by the headset electrodes. In some examples, the signals provided by the body-sense electrodes are inverted and fed into the ground signal, (e.g., to create a driven voltage). In some examples, one or more of the disclosed electrode units are implemented as a ground electrode and/or body-sense electrode.

From the foregoing, it will be appreciated that electrode units have been disclosed that can removably couple to a headset, such as the headset 100 of FIGS. 1-4E. In some examples, the electrode units can be independently removed from the headset to be cleaned, repaired and/or replaced, for example. Additionally, because the electrode units are not fixedly attached to the headset, the electrode units can be easily removed if caught or snagged on a foreign object (e.g., hair), thereby reducing the risk of injury to the subject or damage to the headset. Further, some example electrodes disclosed herein are manufactured by stamping the electrodes from a substrate, such as, for example metals or alloys. Therefore, the electrodes can be manufactured relatively quickly and for low cost.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. An electrode unit comprising:
   a housing having a cavity defined by an opening in a side of the housing; and
   an electrode constructed of a conductive material, the electrode including:
   a ring disposed in the opening; and an arm coupled to the ring, the arm having:
a first end coupled to the ring;
a second end opposite the first end;
a bend between the first end and the second end;
a first portion between the first end and the bend, the first portion extending outward from the opening away from the housing; and
a second portion between the bend and the second end, the second portion extending from the bend toward the housing and into the cavity.

2. The electrode unit of claim 1, wherein the first portion of the arm extends through the ring and outward from the opening away from the housing.

3. The electrode unit of claim 2, wherein the second portion of the arm extends through the ring and into the cavity.

4. The electrode unit of claim 1, wherein the cavity includes a channel extending into the housing.

5. The electrode unit of claim 4, wherein the second portion of the arm is movable into the channel when a force is applied to the bend.

6. The electrode unit of claim 1, further including a connector coupled to the housing around the opening to couple the housing to a band to be worn over a head of a subject.

7. The electrode unit of claim 6, wherein the ring is coupled between the connector and the housing.

8. The electrode unit of claim 6, wherein the connector is a magnet.

9. The electrode unit of claim 1, where the housing further includes a guide, the guide to extend through the ring of the electrode to align the electrode in the housing.

10. The electrode unit of claim 1, wherein the first portion is to move toward the second portion when a force is applied to the bend.

11. The electrode unit of claim 1, wherein the ring and the arm are integral.

12. A headset comprising:
the electrode unit of claim 1; and
a band to be disposed over a head of a subject, the band having an aperture extending through the band, the electrode unit coupled to the band and the first portion of the arm extending through the aperture.

13. The headset of claim 12, wherein the electrode unit further includes a first connector and the band includes a second connector, the first connector to be removably coupled to the second connector.

14. The headset of claim 13, wherein the first connector is a magnet and the second connector is a metal.

15. The headset of claim 14, wherein the second connector is a metal ring disposed around the aperture.

16. An electrode unit comprising:
a housing having a cavity defined by an opening in a side of the housing; and
an electrode constructed of a conductive material, the electrode including:
a ring disposed in the opening; and
an arm coupled to the ring, the arm having:
a first end coupled to the ring;
a second end opposite the first end;
a curve between the first end and the second end;
a first section between the first end and the curve, the first section extending outward from the opening away from the housing; and
a second section between the curve and the second end, the second section extending from the curve toward the housing and into the cavity.

17. The electrode unit of claim 16, wherein the first section of the arm extends through the ring and outward from the opening away from the housing.

18. The electrode unit of claim 17, wherein the second section of the arm extends through the ring and into the cavity.

19. The electrode unit of claim 16, wherein the cavity includes a channel extending into the housing, and wherein the second section of the arm is movable into the channel when a force is applied to the curve.

20. The electrode unit of claim 16, wherein the ring and the arm are integral.

* * * * *